United States Patent
Enomoto

(10) Patent No.: US 11,642,879 B2
(45) Date of Patent: *May 9, 2023

(54) LITHOGRAPHIC PRINTING PLATE PRECURSOR, METHOD FOR PRODUCING LITHOGRAPHIC PRINTING PLATE, AND COLOR-DEVELOPING COMPOSITION

(71) Applicant: FUJIFILM Corporation, Tokyo (JP)

(72) Inventor: Kazuaki Enomoto, Shizuoka (JP)

(73) Assignee: FUJIFITM Corporation, Tokyo (JP)

( * ) Notice: Subject to any disclaimer, the term of this patent is extended or adjusted under 35 U.S.C. 154(b) by 137 days.

This patent is subject to a terminal disclaimer.

(21) Appl. No.: 16/745,372

(22) Filed: Jan. 17, 2020

(65) Prior Publication Data

US 2020/0147951 A1 May 14, 2020

Related U.S. Application Data

(63) Continuation of application No. PCT/JP2018/026238, filed on Jul. 11, 2018.

(30) Foreign Application Priority Data

Jul. 25, 2017 (JP) ............................ JP2017-143870

(51) Int. Cl.
 *B41C 1/10* (2006.01)
 *G03F 7/031* (2006.01)
 *G03F 7/105* (2006.01)

(52) U.S. Cl.
 CPC ............ *B41C 1/1016* (2013.01); *G03F 7/031* (2013.01); *G03F 7/105* (2013.01)

(58) Field of Classification Search
 CPC .................................................. B41C 2210/04
 See application file for complete search history.

(56) References Cited

U.S. PATENT DOCUMENTS

| | | | |
|---|---|---|---|
| 7,217,500 B2 | 5/2007 | Kunita et al. | |
| 8,927,193 B2 * | 1/2015 | Suzuki ................ | C09B 23/0066 430/270.1 |
| 10,241,400 B2 | 3/2019 | Mizuno et al. | |
| 2003/0154874 A1 | 8/2003 | Yamamoto et al. | |
| 2005/0039620 A1 | 2/2005 | Kakino et al. | |
| 2009/0047599 A1 * | 2/2009 | Horne ................... | G03F 7/3035 430/281.1 |
| 2009/0269699 A1 | 10/2009 | Munnelly et al. | |
| 2010/0075260 A1 | 3/2010 | Sasaki | |
| 2014/0360395 A1 | 12/2014 | Nakamura et al. | |
| 2017/0123315 A1 * | 5/2017 | Mizuno ................ | B41M 5/3333 |
| 2018/0356730 A1 * | 12/2018 | Inasaki ................... | G03F 7/168 |

FOREIGN PATENT DOCUMENTS

| | | | | |
|---|---|---|---|---|
| CN | 1388780 | 1/2003 | | |
| CN | 104159976 | 11/2014 | | |
| EP | 1637324 | 3/2006 | | |
| EP | 2113381 | 11/2009 | | |
| JP | 2005067006 | 3/2005 | | |
| JP | 2005091802 | 4/2005 | | |
| JP | 2006062188 | 3/2006 | | |
| JP | 2010032610 | 2/2010 | | |
| JP | 2010064294 | 3/2010 | | |
| JP | 2010069857 | 4/2010 | | |
| JP | 2013054077 | 3/2013 | | |
| JP | 2015186841 | 10/2015 | | |
| WO | 0211996 | 2/2002 | | |
| WO | WO-2007136051 A1 * | 11/2007 | ........... | C07D 271/12 |
| WO | 2013125323 | 8/2013 | | |
| WO | 2016027886 | 2/2016 | | |
| WO | WO-2016027886 A1 * | 2/2016 | ............. | C09B 23/00 |
| WO | WO-2017141882 A1 * | 8/2017 | ............... | G03F 7/16 |

OTHER PUBLICATIONS

Machine English Transaltion of WO-2007136051-A1 (Year: 2022).*
"International Search Report (Form PCT/ISA/210)"of PCT/JP2018/026238, dated Nov. 9, 2018, with English translation thereof, pp. 1-5.
"Written Opinion of the International Searching Authority (Form PCT/ISA/237)" of PCT/JP2018/026238, dated Nov. 9, 2018, with English translation thereof, pp. 1-7.
"Office Action of Japan Counterpart Application", dated Oct. 20, 2020, with English translation thereof, p. 1-p. 13.
"Search Report of Europe Counterpart Application", dated Jul. 27, 2020, p. 1-p. 5.
"Office Action of China Counterpart Application", dated Dec. 28, 2022, with English translation thereof, p. 1-p. 21.

* cited by examiner

*Primary Examiner* — Chanceity N Robinson
(74) *Attorney, Agent, or Firm* — JCIPRNET

(57) ABSTRACT

Provided are a lithographic printing plate precursor comprising: an image-recording layer on a support, in which the image-recording layer includes a dye compound having a decomposable group that is decomposed by an acid, heat, or both and a structure in which decomposition of the decomposable group opens a ring or desorbs a leaving group and an electron-donating polymerization initiator, a method for producing a lithographic printing plate in which the lithographic printing plate precursor is used, and a color-developing composition including a dye compound having a decomposable group that is decomposed by an acid, heat, or both and a structure in which decomposition of the decomposable group opens a ring or desorbs a leaving group and an electron-donating polymerization initiator.

14 Claims, No Drawings

LITHOGRAPHIC PRINTING PLATE PRECURSOR, METHOD FOR PRODUCING LITHOGRAPHIC PRINTING PLATE, AND COLOR-DEVELOPING COMPOSITION

CROSS-REFERENCE TO RELATED APPLICATIONS

This application is a Continuation of International Application No. PCT/JP2018/026238 filed on Jul. 11, 2018, which claims priority to Japanese Patent Application No. 2017-143870 filed on Jul. 25, 2017. The entire contents of these applications are incorporated herein by reference.

BACKGROUND OF THE INVENTION

1. Field of the Invention

The present disclosure relates to a lithographic printing plate precursor, a method for producing a lithographic printing plate, and a color-developing composition.

2. Description of the Related Art

Generally, a lithographic printing plate consists of a lipophilic image area that receives ink in a printing process and a hydrophilic non-image area that receives dampening water. Lithographic printing is a method in which the properties of water and oil-based ink that repel each other are used, the lipophilic image area of the lithographic printing plate is used as an ink-receiving portion, the hydrophilic non-image area is used as a dampening water-receiving portion (non-ink-receiving portion), a difference in the adhesive property of ink is caused on the surface of the lithographic printing plate, the ink is absorbed only in the image area, and then the ink is transferred to a body to be printed such as paper, thereby carrying out printing.

In order to produce this lithographic printing plate, in the related art, a lithographic printing plate precursor (PS plate) formed by providing a lipophilic photosensitive resin layer (image-recording layer) on a hydrophilic support has been broadly used. Generally, a plate is made using a method in which a lithographic printing plate precursor is exposed to light through an original drawing such as a lith film, a portion which is to be an image area of the image-recording layer is left, the other unnecessary portion of the image-recording layer is dissolved and removed using an alkaline developer or an organic solvent, and a hydrophilic surface of a support is exposed, thereby forming a non-image area and a lithographic printing plate is obtained.

In addition, in response to the intensifying interest in the global environment, an environmental issue of waste liquid generated by wet processes such as a development process has gathered more attention.

Regarding the above-described environmental issue, an attempt is made to simplify development or plate production or remove processes. As one of simple production methods, a method called "on-machine development" is being carried out. That is, in the method, after being exposed, a lithographic printing plate precursor is immediately mounted in a printer without being developed as in the related art, and an unnecessary portion of the image-recording layer is removed in an initial phase of an ordinary printing step.

As lithographic printing plate precursors of the related art, for example, lithographic printing plate precursors described in JP2010-064294A or JP2005-091802A are exemplified.

JP2010-064294A describes a printing plate material having at least an image-forming layer on a base material, in which the image-forming layer or other constituent layer contains the following dye precursor A and a photothermal conversion material.

The dye precursor A is a particulate solid, the particle diameter of the dye precursor A is in a range of 0.05 to 2 μm, and the color differs in a non-molten state and in a re-solidified state after being heated and molten.

JP2005-091802A describes a positive-type lithographic printing plate precursor for an infrared laser including (A) a water-insoluble and alkali-soluble resin, (B) an infrared-absorbing dye, and (C) a compound represented by General Formula (I) on a support having a hydrophilic surface and having a thennosensitive layer having a solubility in an alkaline aqueous solution which increases by exposure to an infrared laser.

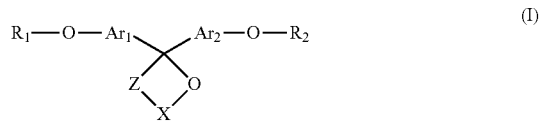

In the formula, $Ar_1$ and $Ar_2$ represent a divalent arylene group which may have a substituent. $R_1$ and $R_2$ each are independently a group that can be decomposed by the action of heat or an acid and represent a group that converts $Ar_1$—O—$R_1$ and $Ar_e$—O—$R_2$ to $Ar_1$—OH and $Ar_e$-OH by decomposition. X is —CO— or —$SO_2$—, and Z represents a divalent alkylene group, cycloalkylene group, alkenylene group, or arylene group. $Ar_1$ and $Ar_e$ may bond to each other through an oxygen atom.

SUMMARY OF THE INVENTION

As a result of intensive studies, the present inventors found that, although it is known that the addition of a leuco dye to a lithographic printing plate precursor improves the color developability, the lithographic printing plate precursor fades over time, and there is a problem with the temporal fading-suppressing property.

An object that an embodiment of the present invention attempts to achieve is to provide a lithographic printing plate precursor being excellent in terms of color developability and a temporal fading-suppressing property.

Another object that another embodiment of the present invention attempts to achieve is to provide a method for producing a lithographic printing plate in which the lithographic printing plate precursor is used.

Still another object that still another embodiment of the present invention attempts to achieve is to provide a color-developing composition being excellent in terms of color developability and a temporal fading-suppressing property.

Means for achieving the above-described objects includes the following aspects.

<1> A lithographic printing plate precursor comprising: an image-recording layer on a support, in which the image-recording layer includes a dye compound having a decomposable group that is decomposed by an acid, heat, or both and a structure in which decomposition of the decomposable group opens a ring or desorbs a leaving group and an electron-donating polymerization initiator.

<2> The lithographic printing plate precursor according to <1>, in which the decomposable group is a group that is decomposed by an acid, heat, or both to generate an amino group or a hydroxy group.

<3> The lithographic printing plate precursor according to <1> or <2>, in which the structure in which decomposition of the decomposable group opens a ring or desorbs a leaving group is a structure represented by any of Formula 1a to Formula 1d.

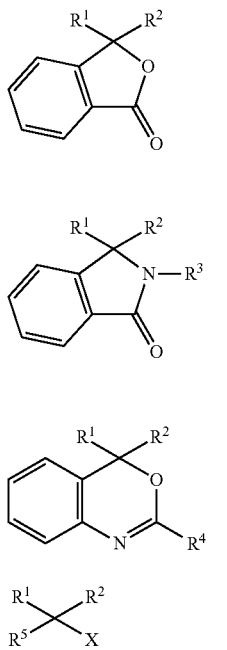

(1a)

(1b)

(1c)

(1d)

In Formula 1a to Formula 1d, $R^1$ and $R^2$ represent a portion that is linked to a core structure of the dye compound, $R^3$ and $R^4$ represent an aryl group or a heteroaryl group, $R^5$ represents a hydrocarbon group, and X represents the leaving group.

<4> The lithographic printing plate precursor according to any one of <1> to <3>, in which the decomposable group is a group represented by Formula 2a or Formula 2b.

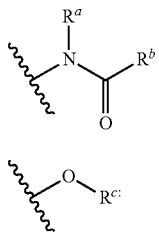

(2a)

(2b)

In Formula 2a and Formula 2b, $R^a$ represents a hydrogen atom or an alkyl group, $R^b$ represents a hydrogen atom, an alkyl group, an aryl group, a heteroaryl group, an alkoxy group, or an aryloxy group, $R^c$ represents a protective group for a hydroxy group, and a wavy portion represents a bonding position with other structures.

<5> The lithographic printing plate precursor according to any one of <1> to <4>, in which the dye compound has a structure represented by any of Formula 3a to Formula 3d as a core structure.

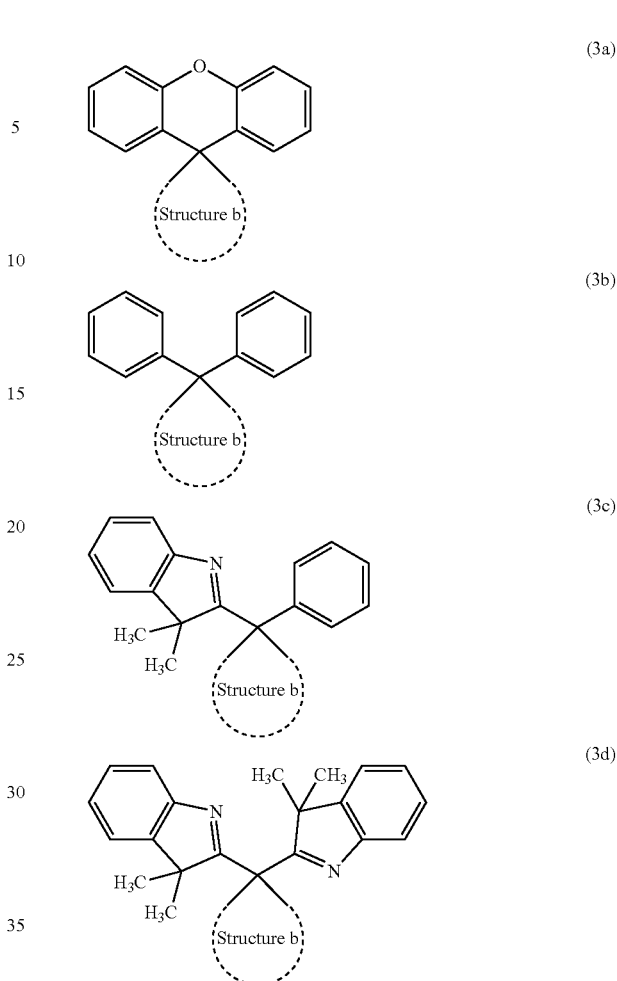

(3a)

(3b)

(3c)

(3d)

In Formula 3a to Formula 3d, a structure b represents a structure in which a ring is opened by decomposition of the decomposable group, and the structures represented by Formula 3a to Formula 3d have one or more decomposable groups on an aromatic ring in Formula 3a to Formula 3d.

<6> The lithographic printing plate precursor according to any one of <1> to <5>, in which the electron-donating polymerization initiator is a borate compound.

<7> The lithographic printing plate precursor according to any one of <1> to <6>, in which the image-recording layer further includes an infrared absorber.

<8> The lithographic printing plate precursor according to <7>, in which the infrared absorber is a cyanine colorant.

<9> The lithographic printing plate precursor according to any one of <1> to <8>, in which the image-recording layer further includes an electron-receiving polymerization initiator.

<10> The lithographic printing plate precursor according to any one of <1> to <9>, in which the image-recording layer further includes a polymer particle.

<11> The lithographic printing plate precursor according to any one of <1> to <10>, in which the image-recording layer further includes a polymerizable compound.

<12> The lithographic printing plate precursor according to any one of <1> to <11>, in which the image-recording layer further includes a binder polymer.

<13> A method for producing a lithographic printing plate, comprising: a step of exposing the lithographic printing plate precursor according to any one of <1> to <12> in an image shape and forming an exposed portion and a non-exposed portion; and a step of removing the non-exposed portion by supplying at least one of printing ink or dampening water.

<14> A color-developing composition comprising: a dye compound having a decomposable group that is decomposed by an acid, heat, or both and a structure in which decomposition of the decomposable group opens a ring or desorbs a leaving group; and an electron-donating polymerization initiator.

According to the embodiment of the present invention, it is possible to provide a lithographic printing plate precursor being excellent in terms of color developability and a temporal fading-suppressing property.

According to another embodiment of the present invention, it is possible to provide a method for producing a lithographic printing plate in which the lithographic printing plate precursor is used.

According to still another embodiment of the present invention, it is possible to provide a color-developing composition being excellent in terms of color developability and a temporal fading-suppressing property.

DESCRIPTION OF THE PREFERRED EMBODIMENTS

Hereinafter, the contents of the present disclosure will be described in detail. Constituent requirements mentioned below will be described on the basis of typical embodiments of the present disclosure, but the present disclosure is not limited to such embodiments.

Meanwhile, in the present specification, a numerical range expressed using "to" includes numerical values described before and after "to" as the lower limit value and the upper limit value.

In addition, in the present specification, a group (atomic group) that is not expressed whether the group is substituted or not substituted refers to both a group not having a substituent and a group having a substituent. For example, an "alkyl group" refers not only to an alkyl group not having a substituent (unsubstituted alkyl group) but also to an alkyl group having a substituent (substituted alkyl group).

In the present specification, "(meth)acryl" is an expression used with a concept of including both acryl and methacryl, and "(meth)acryloyl" is an expression used with a concept of including both acryloyl and methacryloyl.

In addition, the term "step" in the present specification refers not only to an independent step but also a step that cannot be clearly differentiated from other steps as long as the intended purpose of the step is achieved. In addition, in the present disclosure, "% by mass" and "% by weight" have the same meaning, and "parts by mass" and "parts by weight" have the same meaning.

Furthermore, in the present disclosure, a combination of two or more preferred aspects is a more preferred aspect.

In addition, unless particularly otherwise described, the weight-average molecular weight (Mw) and the number average molecular weight (Mn) in the present disclosure refer to a molecular weight that is detected using a gel permeation chromatography (GPC) analyzer in which columns of TSKgel GMHxL, TSKgel G4000HxL, and TSKgel G2000HxL (all are trade names manufactured by Tosoh Corporation) are used, solvent tetrahydrofuran (THF), and a differential refractometer and is converted using polystyrene as a standard substance.

In the present specification, the term "lithographic printing plate precursor" refers not only to a lithographic printing plate precursor but also to a key plate precursor. In addition, the term "lithographic printing plate" refers not only to a lithographic printing plate produced by carrying out operations such as exposure and development as necessary on the lithographic printing plate precursor but also to a key plate. In the case of the key plate precursor, the operations such as exposure and development are not necessarily required. Meanwhile, the key plate refers to a lithographic printing plate precursor intended to be attached to a plate cylinder that is not used in a case in which monochromatic or dichromatic printing is carried out on a part of paper during, for example, color newspaper printing.

Hereinafter, the present disclosure will be described in detail.

(Lithographic Printing Plate Precursor)

A lithographic printing plate precursor according to an embodiment of the present disclosure has an image-recording layer on a support, and the image-recording layer includes a dye compound having a decomposable group that is decomposed by an acid, heat, or both and a structure in which decomposition of the decomposable group opens a ring or desorbs a leaving group (hereinafter, also referred to as the "specific dye compound") and an electron-donating polymerization initiator.

In addition, the lithographic printing plate precursor according to the embodiment of the present disclosure can be preferably used as a lithographic printing plate precursor for on-machine development.

As described above, the present inventors found that, in lithographic printing plate precursors of the related art, it is known that the addition of a leuco dye to a lithographic printing plate precursor improves the color developability, but the lithographic printing plate precursor fades over time, and there is a problem with the temporal fading-suppressing property.

In generally-known leuco dyes of the related art, as described below, a decoloring body and a color developing body have an equilibrium relationship, and thus it is assumed that the color developability decreases as the time elapses.

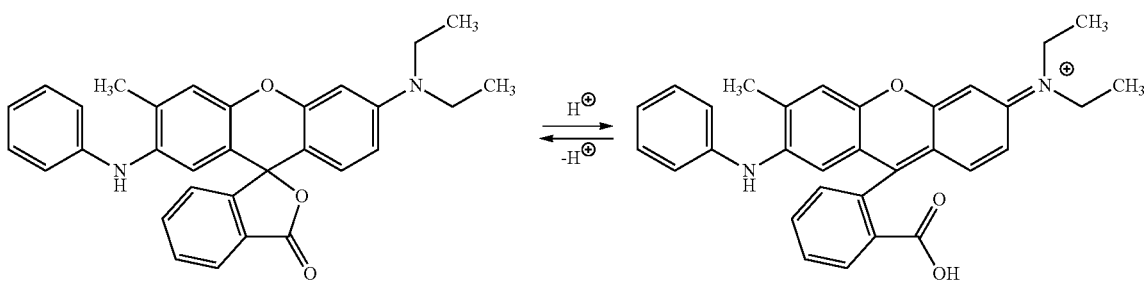

Therefore, the present inventors carried out detailed studies and considered that it is possible to suppress decoloration over time using a dye compound that irreversibly generates a color developing body (that is decomposed to generate a color developing body), specifically, a dye compound having a decomposable group that is decomposed by an acid, heat, or both and a structure in which decomposition of the decomposable group opens a ring or desorbs a leaving group. An example of the color development mechanism of the specific dye compound will be illustrated below.

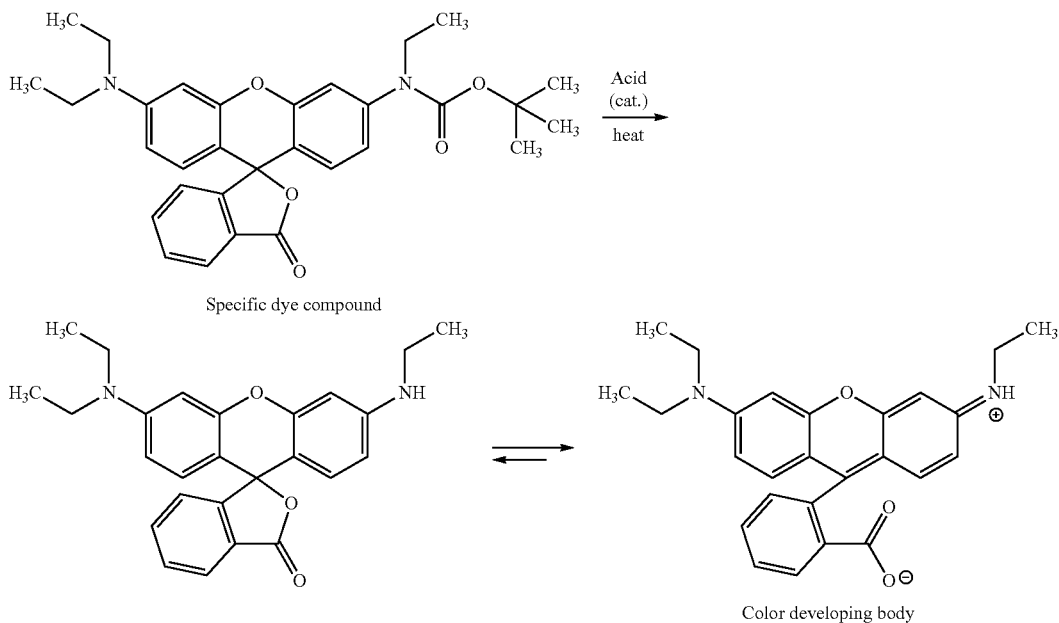

In addition, the detailed mechanism is not clear, but the present inventors found that, in the case of jointly using the specific dye compound and the electron-donating polymerization initiator, it is possible to improve the decomposition efficiency of the specific dye compound and develop strong color developability.

It is assumed that the electron-donating polymerization initiator does not only accelerate the decomposition of the decomposable group in the specific dye compound but also accelerates the ring opening in the specific dye compound or the desorption of the leaving group, whereby the color developability improves.

<Image-Recording Layer>

The lithographic printing plate precursor according to the embodiment of the present disclosure has an image-recording layer on a support, and the image-recording layer includes a dye compound having a decomposable group that is decomposed by an acid, heat, or both and a structure in which decomposition of the decomposable group opens a ring or desorbs a leaving group (hereinafter, also referred to as the "specific dye compound") and an electron-donating polymerization initiator.

The image-recording layer that is used in the present disclosure is preferably a negative-type image-recording layer and more preferably a water-soluble or water-dispersive negative-type image-recording layer.

In addition, the image-recording layer that is used in the present disclosure preferably further includes an electron-receiving polymerization initiator and a polymerizable compound from the viewpoint of printing resistance and photosensitivity.

From the viewpoint of on-machine developability, in the lithographic printing plate precursor of the embodiment of the present disclosure, a non-exposed portion of the image-recording layer preferably can be removed by at least any of dampening water or printing ink.

Hereinafter, individual components that are included in the image-recording layer will be described in detail.

—Specific Dye Compound—

The image-recording layer in the lithographic printing plate precursor according to the embodiment of the present disclosure includes a dye compound having a decomposable group that is decomposed by an acid, heat, or both and a structure in which decomposition of the decomposable group opens a ring or desorbs a leaving group (specific dye compound).

The decomposable group needs to be a group that is decomposed by an acid, heat, or both and is preferably a group that is decomposed by at least an acid from the viewpoint of color developability.

The acid may be a protonic acid or a Lewis acid.

In addition, the heat is preferably heat of 80° C. or higher and 200° C. or lower and more preferably heat of 100° C. or higher and 180° C. or lower.

From the viewpoint of color developability and a temporal fading-suppressing property, the decomposable group is preferably a group that is decomposed by an acid, heat, or both to generate an amino group or a hydroxy group and more preferably a group that is decomposed by an acid, heat, or both to generate an amino group.

In addition, the amino group that is generated by the decomposition of the decomposable group may be an unsubstituted amino group or a monosubstituted amino group, but is preferably a monosubstituted amino group and more preferably an alkylamino group from the viewpoint of color developability and a temporal fading-suppressing property.

In addition, from the viewpoint of color developability and a temporal fading-suppressing property, the decomposable group is preferably a group represented by Formula 2a or Formula 2b and more preferably a group represented by Formula 2a.

In Formula 2a and Formula 2b, $R^a$ represents a hydrogen atom or an alkyl group, $R^b$ represents a hydrogen atom, an alkyl group, an aryl group, a heteroaryl group, an alkoxy group, or an aryloxy group, $R^e$ represents a protective group for a hydroxy group, and a wavy portion represents a bonding position with other structures.

From the viewpoint of color developability and a temporal fading-suppressing property, $R^a$ is preferably an alkyl group, more preferably an alkyl group having 1 to 8 carbon atoms, still more preferably an alkyl group having 1 to 4 carbon atoms, and particularly preferably a methyl group or an ethyl group.

From the viewpoint of color developability and a temporal fading-suppressing property, $R^b$ is preferably an alkoxy group or an aryloxy group, more preferably an alkoxy group, and still more preferably a tertiary alkoxy group, an aryl methoxy group, or a 2-trialkylsilyl ethoxy group.

From the viewpoint of color developability and a temporal fading-suppressing property, $R^e$ is preferably an acetal protective group, an oxycarbonyl protective group, an acyl group, or a silyl group, more preferably a tetrahydrofuranyl group, a tetrahydropyranyl group, a 1-alkoxyalkyl group, a tertiary alkoxycarbonyl group, an acyl group, or a trialkylsilyl group, still more preferably a tetrahydrofuranyl group, a tetrahydropyranyl group, a 1-alkoxyalkyl group, a tertiary alkoxycarbonyl group, or a trialkylsilyl group, and particularly preferably a tetrahydrofuranyl group, a tetrahydropyranyl group, or a trialkylsilyl group.

The specific dye compound needs to have one or more decomposable groups, but the number of the decomposable groups in the specific dye compound is preferably 1 to 4, more preferably 1 or 2, and particularly preferably 1 from the viewpoint of color developability.

In addition, from the viewpoint of color developability and a temporal fading-suppressing property, the decomposable group is preferably a group having at least one structure selected from the group consisting of a urethane bond and a carbonate bond.

In addition, the Hammett value of the group that is generated by the decomposition of the decomposable group is preferably 0 or less, more preferably −0.3 or less, and still more preferably −1.0 or more and −0.5 or less.

A method for computing the iHammett value of the group in the present disclosure is based on Chem. Rev., 1991, 97, 165-195. For example, a para position and a meta position in each of the core structures described below are defined as described below.

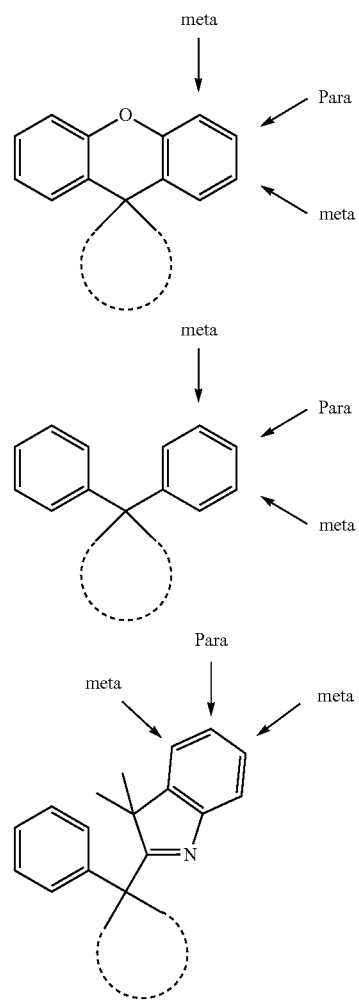

In the case of computing the Hammett value of a group that is not described in the above-described document, a value that is conveniently computed from the following expression using an equilibrium constant pKx of a corresponding substituted benzoic acid at 25° C. and an equilibrium constant $pK_H$ of an unsubstituted benzoic acid (4.201) (J. Org. Chem., 1958, 23(3), pp. 420 to 427).

$$\sigma = pKx - pK_H$$

As the value of the substituted benzoic acid, a value known as a literature datum may be used or the value may be experimentally computed using a method described below.

The corresponding substituted benzoic acid is added to a solution of ethanol and water (50/50), titration is carried out using a 0.1 N NaOH aqueous solution at 25° C., and pKx is computed from pH at the half neutralization point. The substituted benzoic acid is a weak acid, and thus pH may be regarded to be identical to pKx at the half neutralization point.

From the viewpoint of color developability and a temporal fading-suppressing property, as the decomposable group, specifically, groups represented by any of Formula D-1 to Formula D-5 are preferably exemplified, groups represented by any of Formula D-1 to Formula D-4 are more preferably exemplified, groups represented by any of Formula D-1 to Formula D-3 are still more preferably exemplified, and a group represented by Formula D-1 is preferably exemplified. A wavy portion represents a bonding position with other structures.

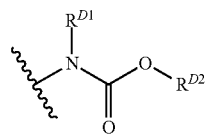

(D-1)

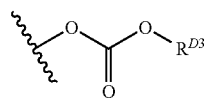

(D-2)

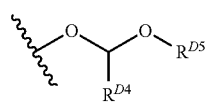

(D-3)

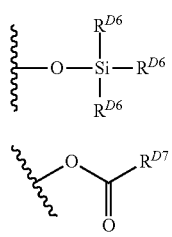

(D-4)

(D-5)

In Formula D-1 to Formula D-5, $R^{D1}$ represents an alkyl group, $R^{D2}$ represents an alkyl group or an aryl group, $R^{D3}$ represents an alkyl group, $R^{D4}$ represents a hydrogen atom or an alkyl group, $R^{D5}$ represents an alkyl group, $R^{D4}$ and $R^{D5}$ may bond to each other to form a ring, $R^{D6}$'s each independently represent an alkyl group or an aryl group, and $R^{D7}$ represents an alkyl group or an aryl group.

From the viewpoint of color developability and a temporal fading-suppressing property, $R^{D1}$ is preferably an alkyl group having 1 to 8 carbon atoms, more preferably an alkyl group having 1 to 4 carbon atoms, and particularly preferably a methyl group or an ethyl group.

From the viewpoint of color developability and a temporal fading-suppressing property, $R^{D2}$ is preferably an alkyl group and more preferably a tertiary alkyl group, aryl methyl group, or 2-trialkylsilyl ethyl group.

From the viewpoint of color developability and a temporal fading-suppressing property, $R^{D3}$ is preferably a tertiary alkyl group.

From the viewpoint of color developability and a temporal fading-suppressing property, $R^{D4}$ and $R^{D5}$ preferably bond to each other to form a ring and more preferably bond to each other to form a five- or six-membered ring.

In addition, from the viewpoint of color developability and a temporal fading-suppressing property, an aspect in which $R^{D4}$ is a hydrogen atom and $R^{D5}$ is an alkyl group is also preferred.

From the viewpoint of color developability and a temporal fading-suppressing property, $R^{D6}$'s each are independently preferably an alkyl group and particularly preferably a methyl group.

From the viewpoint of color developability and a temporal fading-suppressing property, $R^{D7}$ is preferably an alkyl group, more preferably an alkyl group having 1 to 4 carbon atoms, and still more preferably a methyl group.

The structure in which the decomposition of the decomposable group opens a ring or desorbs a leaving group is preferably a structure in which the decomposition of the decomposable group opens a ring from the viewpoint of color developability.

In addition, in the specific dye compound, from the viewpoint of color developability and a temporal fading-suppressing property, the portion in which a ring is opened or a leaving group is desorbed is preferably a compound having a quaternary carbon atom in which three carbon atoms and one hetero atom (preferably a nitrogen atom or an oxygen atom and more preferably an oxygen atom) bond to each other.

From the viewpoint of color developability and a temporal fading-suppressing property, as the structure in which the decomposition of the decomposable group opens a ring or desorbs a leaving group, a structure represented by any of Formula 1a to Formula 1d is preferred, a structure represented by any of Formula 1a to Formula 1c is more preferred, and a structure represented by Formula 1a is particularly preferred.

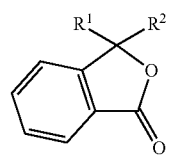

(1a)

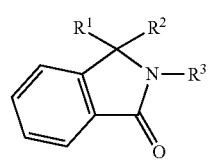

(1b)

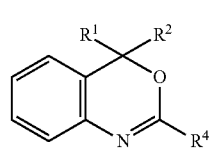

(1c)

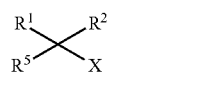

(1d)

In Formula 1a to Formula 1 d, $R^1$ and $R^2$ represent a portion that is linked to a core structure of the dye compound, $R^3$ and $R^4$ represent an aryl group or a heteroaryl group, $R^5$ represents a hydrocarbon group, and X represents the leaving group.

From the viewpoint of color developability, $R^3$ and $R^4$ is preferably an aryl group having 6 to 12 carbon atoms or a heteroaryl group having 2 to 12 carbon atoms, more preferably an aryl group having 6 to 12 carbon atoms, and still more preferably a phenyl group.

From the viewpoint of color developability, $R^5$ is preferably an alkyl group or an aryl group, more preferably an aryl group, still more preferably an aryl group having 6 to 12 carbon atoms, and particularly preferably a phenyl group.

X is not particularly limited as long as X is a group that can be desorbed by the decomposition of the decomposable group, but is preferably an acyloxy group, more preferably an acyloxy group having 1 to 8 carbon atoms, and still more preferably an acetyloxy group.

From the viewpoint of color developability, as the core structure, the specific dye compound preferably has a structure represented by any of Formula 3a to Formula 3d and more preferably has the structure represented by Formula 3a.

(3a)

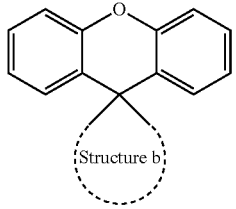

(3b)

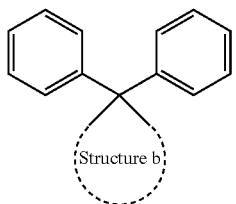

(3c)

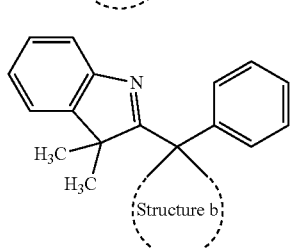

(3d)

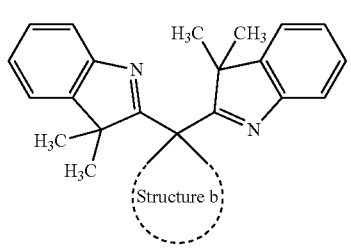

In Formula 3a to Formula 3d, a structure b represents a structure in which a ring is opened by the decomposition of the decomposable group, and the structures represented by Formula 3a to Formula 3d have one or more decomposable groups described above on an aromatic ring in Formula 3a to Formula 3d.

From the viewpoint of color developability and a temporal fading-suppressing property, the structure b is preferably a structure represented by any of Formula 1a to Formula 1d.

The structures represented by Formula 3a to Formula 3d have one or more decomposable groups described above on an aromatic ring in Formula 3a to Formula 3d and, furthermore, may have a substituent on the aromatic ring.

As the substituent, an alkyl group, an aryl group, an alkoxy group, an aryloxy group, a dialkylamino group, a diarylamino group, an alkylarylamino group, an arylamino group, an alkylamino group, and the like are preferably exemplified.

Among them, from the viewpoint of color developability and a temporal fading-suppressing property, the structures preferably have at least one dialkylamino group as the substituent.

From the viewpoint of color developability and a temporal fading-suppressing property, the specific dye compound is particularly preferably a compound represented by Formula D-6.

(D-6)

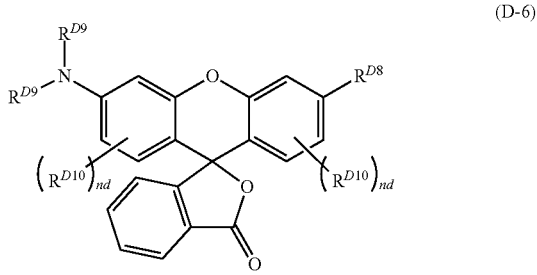

In Formula D-6, $R^{D8}$ represents the decomposable group, $R^{D9}$'s each independently represent an alkyl group or an aryl group, $R^{D10}$'s each independently represent an alkyl group or an aryl group, and nd's each independently represent an integer of 0 to 3.

From the viewpoint of color developability and a temporal fading-suppressing property, $R^{D9}$'s each are independently preferably an alkyl group having 1 to 12 carbon atoms or an aryl group having 6 to 12 carbon atoms, more preferably an alkyl group having 1 to 4 carbon atoms, a benzyl group, or a phenyl group, and still more preferably an alkyl group having 1 to 4 carbon atoms.

$R^{D10}$'s each are independently preferably an alkyl group and more preferably a methyl group.

nd's each are independently preferably 0 or 1 and more preferably 0.

Hereinafter, as preferred specific examples of the specific dye compound, dye compounds 1 to 21 will be illustrated, but it is needless to say that the specific dye compound is not limited thereto. Ph represents a phenyl group.

-continued
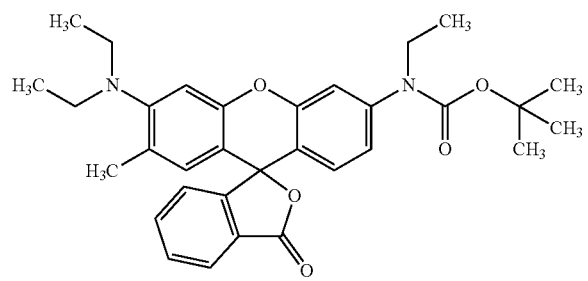
NH(CH₃CH₃) group after decomposition
σρ = −0.61
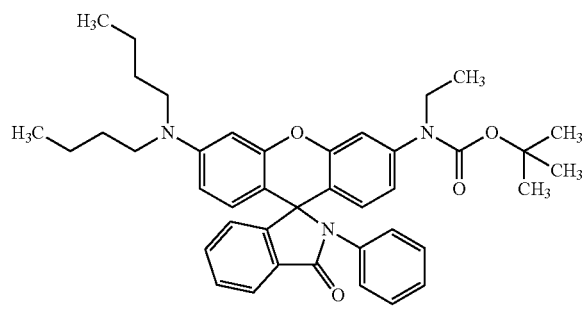
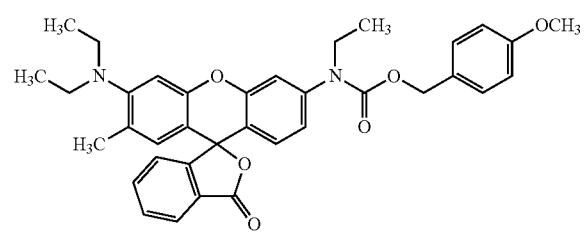
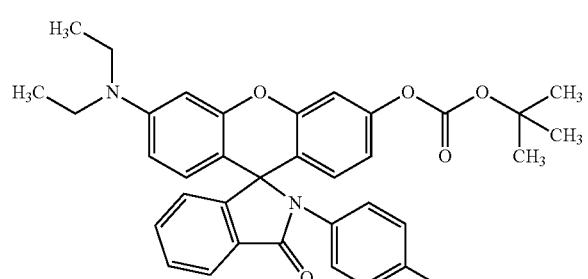
OH group after decomposition
σρ = −0.37
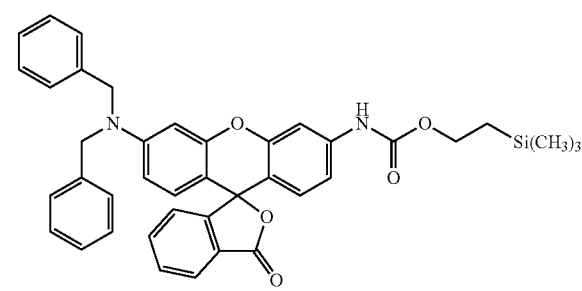
NH₂ group after decomposition
σρ = −0.66
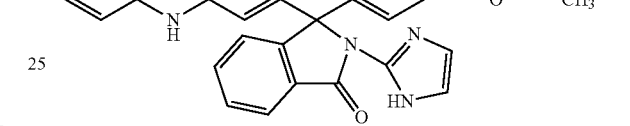
NHCH₃ group after decomposition
σρ = −0.70
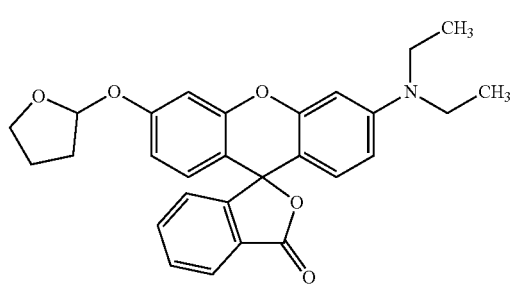
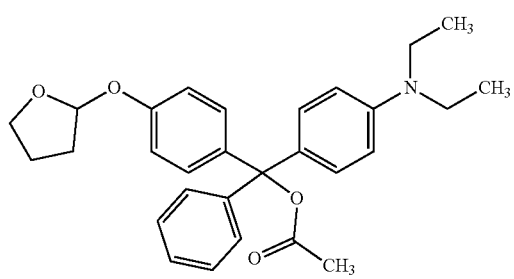
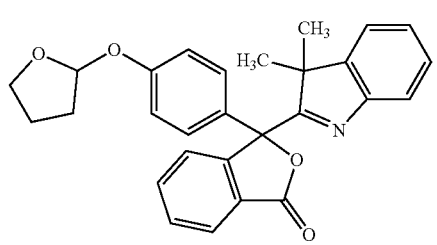

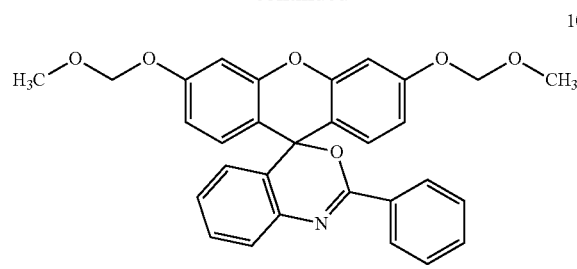
10
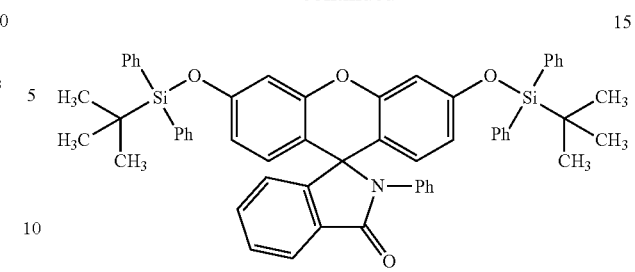
15
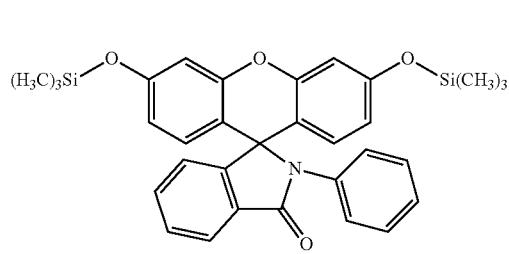
11
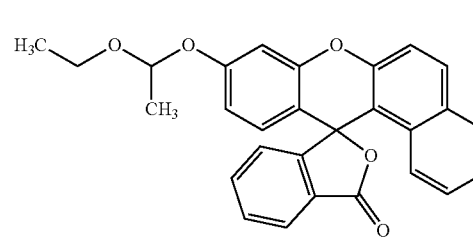
16
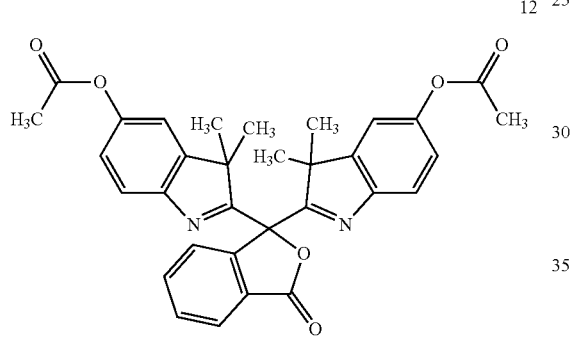
12
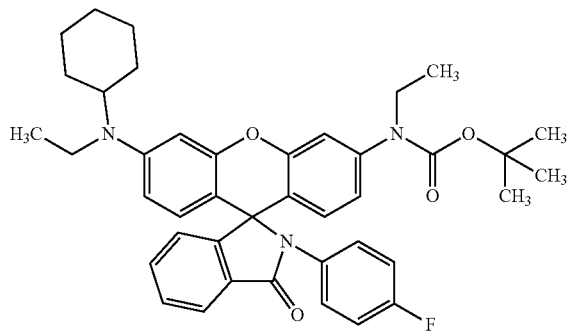
17
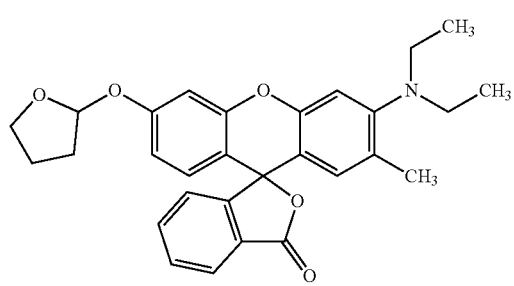
13
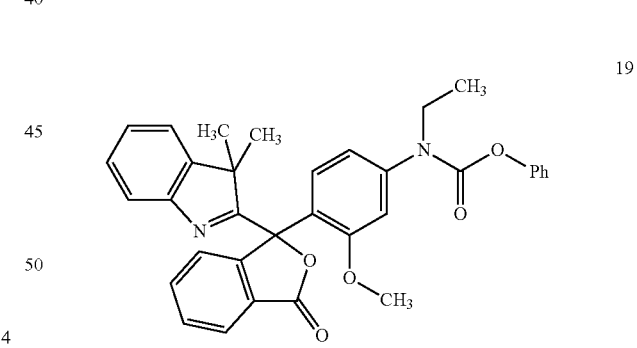
18
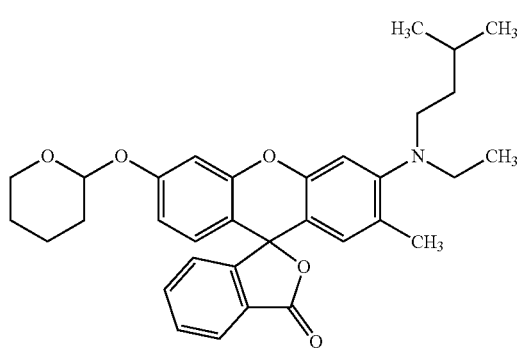
14
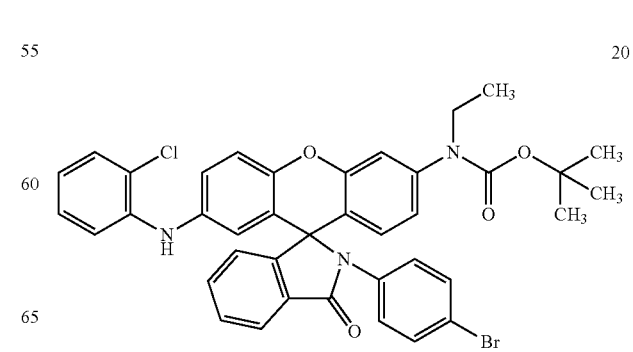
19
20

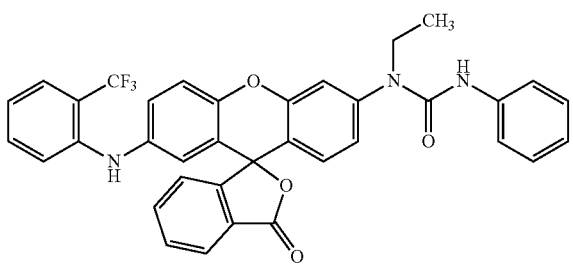

21

A method for producing the specific dye compound is not particularly limited, and it is possible to produce the specific dye compound with reference to a well-known method for producing a leuco dye, a method for introducing a decomposable group, or the like.

The specific dye compound may be used singly, and it is also possible to jointly use two or more components in combination.

From the viewpoint of color developability and the temporal fading-suppressing property, the content of the specific dye compound is preferably 0.1% by mass to 20% by mass, more preferably 0.5% by mass to 10% by mass, and still more preferably 1% by mass to 5% by mass of the total mass of the image-recording layer.

—Electron-Donating Polymerization Initiator—

The image-recording layer in the lithographic printing plate precursor according to the embodiment of the present disclosure includes an electron-donating polymerization initiator.

The electron-donating polymerization initiator in the present disclosure is a compound that generates a polymerization initiating species such as a radical by donating one electron to an orbit of the infrared-absorbing dye from which one electron is removed through intermolecular electron migration in a case in which the electron of the infrared-absorbing dye is excited by exposure to an infrared ray or migrates in the molecule.

As the electron-donating polymerization initiator, an electron-donating radical polymerization initiator is preferred.

The image-recording layer more preferably contains an electron-donating polymerization initiator described below from the viewpoint of improving the printing resistance of lithographic printing plates, and, as examples thereof, the following five kinds are exemplified.

(i) Alkyl or arylate complex: It is considered that a carbon-hetero bond is oxidatively cleaved, and an active radical is generated. Specifically, a borate compound is preferred.

(ii) N-arylalkylamine compound: It is considered that a C—X bond on carbon adjacent to nitrogen is cleaved by oxidation, and an active radical is generated. As X, a hydrogen atom, a carboxyl group, a trimethylsilyl group, or a benzyl group is preferred. Specifically, for example, N-phenylglycines (which may or may not have a substituent in a phenyl group) and N-phenyl iminodiacetic acid (which may or may not have a substituent in a phenyl group) are exemplified.

(iii) Sulfur-containing compound: A compound in which a nitrogen atom in the above-described amines is substituted into a sulfur atom is capable of generating an active radical by the same action. For example, phenylthioacetic acid (which may or may not have a substituent in a phenyl group) is exemplified.

(iv) Tin-containing compound: A compound in which a nitrogen atom in the above-described amines is substituted into a tin atom is capable of generating an active radical by the same action.

(v) Sulfinates: Sulfinates are capable of generating an active radical by oxidation. Specifically, sodium arylsulfinate and the like can be exemplified.

Among these, from the viewpoint of printing resistance and color developability, the image-recording layer preferably contains a borate compound.

From the viewpoint of printing resistance and color developability, the borate compound is preferably a tetraaryl borate compound or a monoalkyltriaryl borate compound and more preferably a tetraaryl borate compound.

A counter cation that the borate compound has is not particularly limited, but is preferably an alkali metal ion or a tetraalkyl ammonium ion and more preferably a sodium ion, a potassium ion, or a tetrabutylammonium ion.

As the borate compound, specifically, sodium tetraphenyl borate is preferably exemplified.

Hereinafter, as preferred specific examples of the electron-donating polymerization initiator, B-1 to B-9 will be illustrated, but it is needless to say that the electron-donating polymerization initiator is not limited thereto. In addition, in the following chemical formulae, Ph represents a phenyl group, and Bu represents an n-butyl group.

B-1
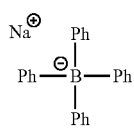

B-2
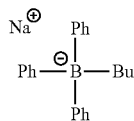

B-3
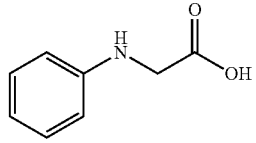

B-4
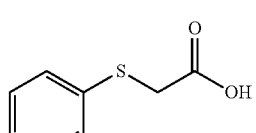

B-5
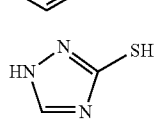

B-6
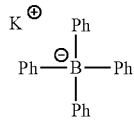

B-7
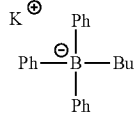

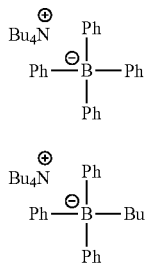

B-8

B-9

Only one electron-donating polymerization initiator may be added or two or more electron-donating polymerization initiators may be jointly used.

From the viewpoint of color developability and the temporal fading-suppressing property, the content of the electron-donating polymerization initiator is preferably 0.01% by mass to 30% by mass, more preferably 0.05% by mass to 25% by mass, and still more preferably 0.1% by mass to 20% by mass of the total mass of the image-recording layer.

In addition, from the viewpoint of color developability and the temporal fading-suppressing property, the contained mass ratio between the specific dye compound and the electron-donating polymerization initiator in the image-recording layer is preferably 10:1 to 1:10, more preferably 5:1 to 1:5, still more preferably 2:1 to 1:2, and particularly preferably 1.5:1 to 1:1.5 (the specific dye compound: the electron-donating polymerization initiator).

—Infrared Absorber—

The image-recording layer preferably includes an infrared absorber.

As the infrared absorber, pigments and dyes are exemplified.

As the dye that is used as the infrared absorber, it is possible to use a commercially available dye and a well-known dye described in publications, for example, "Dye Handbooks" (edited by the Society of Synthetic Organic Chemistry, Japan and published on 1970). Specific examples thereof include dyes such as an azo dye, a metal complex azo dye, a pyrazolone azo dye, a naphthoquinone dye, an anthraquinone dye, a phthalocyanine dye, a carbonium dye, a quinoneimine dye, a methine dye, a cyanine dye, a squarylium colorant, a pyrylium salt, and a metal thiolate complex.

Among these dyes, as particularly preferred dyes, a cyanine colorant, a squarylium colorant, a pyrylium salt, a nickel thiolate complex, and an indolenine cyanine colorant are exemplified. Furthermore, a cyanine colorant or an indolenine cyanine colorant is exemplified. Between these, a cyanine colorant is particularly preferred.

Specific examples of the cyanine colorant include a compound described in Paragraphs 0017 to 0019 of JP2001-133969A, a compound described in Paragraphs 0016 to 0021 of JP2002-023360A and Paragraphs 0012 to 0037 of JP2002-040638A, preferably a compound described in Paragraphs 0034 to 0041 of JP2002-278057A and Paragraphs 0080 to 0086 of JP2008-195018A, particularly preferably a compound described in Paragraphs 0035 to 0043 of JP2007-090850A, and a compound described in Paragraphs 0105 to 0113 of JP2012-206495A.

In addition, it is also possible to preferably use a compound described in Paragraphs 0008 and 0009 of JP1993-005005A (JP-H05-005005A) and Paragraphs 0022 to 0025 of JP2001-222101A.

As the pigment, a compound described in Paragraphs 0072 to 0076 of JP2008-195018A is preferred.

The infrared absorber may be used singly or two or more infrared absorbers may be jointly used. In addition, a pigment and a dye may be jointly used as the infrared absorber.

The content of the infrared absorber in the image-recording layer is preferably 0.1% by mass to 10.0% by mass and more preferably 0.5% by mass to 5.0% by mass of the total mass of the image-recording layer.

—Electron-Receiving Polymerization Initiator—

The image-recording layer preferably includes an electron-receiving polymerization initiator.

The electron-receiving polymerization initiator is a compound that generates a polymerization initiating species such as a radical by receiving one electron through intermolecular electron migration in a case in which the electron of the infrared absorber is excited by exposure to an infrared ray.

As the electron-receiving polymerization initiator that is used in the present disclosure, it is possible to appropriately select a compound that generates a polymerization initiating species such as a radical or a cation by either or both of light energy and heat energy such as a well-known thermopolymerization initiator, a compound having a bond with a small bond dissociation energy, a photopolymerization initiator, and the like and use the compound.

The electron-receiving polymerization initiator is preferably a radical polymerization initiator and more preferably an onium salt compound.

In addition, as the electron-receiving polymerization initiator, an infrared-ray-sensitive polymerization initiator is preferred.

The electron-receiving polymerization initiator may be used singly or two or more electron-receiving polymerization initiators may be jointly used.

Examples of the electron-receiving radical polymerization initiator include (a) an organic halide, (b) a carbonyl compound, (c) an azo compound, (d) an organic peroxide, (e) a metallocene compound, (f) an azide compound, (g) a hexaarylbiimidazole compound, (i) a disulfone compound, (j) an oxime ester compound, and (k) an onium salt compound.

As the organic halide (a), for example, a compound described in Paragraphs 0022 and 0023 of JP2008-195018A is preferred.

As the carbonyl compound (b), for example, a compound described in Paragraph 0024 of JP2008-195018A is preferred.

As the azo compound (c), for example, an azo compound described in JP1996-108621A (JP-H08-108621A) can be used.

As the organic peroxide (d), for example, a compound described in Paragraph 0025 of JP2008-195018A is preferred.

As the metallocene compound (e), for example, a compound described in Paragraph 0026 of JP2008-195018A is preferred.

As the azide compound (f), for example, a compound such as 2,6-bis(4-azidobenzylidene)-4-methylcyclohexanone can be exemplified.

As the hexaarylbiimidazole compound (g), for example, a compound described in Paragraph 0027 of JP2008-195018A is preferred.

As the disulfone compound (i), for example, a compound described in each of JP1986-166544A (JP-S61-166544A) and JP2002-328465A is exemplified.

As the oxime ester compound (j), for example, a compound described in Paragraphs 0028 to 0030 of JP2008-195018A is preferred.

Among the above-described electron-receiving polymerization initiators, as preferred electron-receiving polymerization initiators, the oxime ester compound and the onium salt compound are exemplified from the viewpoint of a curing property. Between them, from the viewpoint of printing resistance, an iodium salt compound, a sulfonium salt compound, or an azinium salt compound is preferred, an iodium salt compound or a sulfonium salt compound is more preferred, and an iodium salt compound is particularly preferred.

Specific examples of these compounds will be illustrated below, but the present disclosure is not limited thereto.

As an example of the iodonium salt compound, a diaryl iodonium salt compound is preferred, a diphenyl iodonium salt compound substituted with, particularly, an electron-donating group, for example, an alkyl group or an alkoxyl group is more preferred, and an asymmetric diphenyl iodonium salt compound is preferred. Specific examples thereof include diphenyliodonium=hexafluorophosphate, 4-methoxyphenyl-4-(2-methylpropyl)phenyliodonium=hexafluorophosphate, 4-(2-methylpropyl)phenyl-p-tolyliodonium=hexafluorophosphate, 4-hexyloxyphenyl-2,4,6-trimethoxyphenyl iodonium=hexafluorophosphate, 4-hexyloxyphenyl-2,4-di ethoxyphenyl iodonium=tetrafluoroborate, 4-octyloxyphenyl-2,4,6-trimethoxyphenyl iodonium=1-perfluorobutane sulfonate, 4-octyloxyphenyl-2,4,6-trimethoxyphenyliodonium=hexafluorophosphate, and bis(4-t-butylphenyl)iodonium=hexafluorophosphate.

As an example of the sulfonium salt compound, a triarylsulfonium salt compound is preferred, a triarylsulfonium salt compound in which, particularly, an electron-attracting group, for example, at least some of groups on the aromatic ring are substituted with a halogen atom is preferred, and a triarylsulfonium salt compound in which the total number of substituted halogen atoms on the aromatic ring is four or more is more preferred. Specific examples thereof include triphenylsulfonium=hexafluorophosphate, triphenylsulfonium=benzoyl formate, bis(4-chlorophenyl)phenylsulfonium=benzoyl formate, bis(4-chlorophenyl)-4-methylphenylsulfonium=tetrafluoroborate, tris(4-chlorophenyl)sulfonium=3,5-bis(methoxycarbonyl)benzenesulfonate, tris(4-chlorophenyl)sulfonium=hexafluorophosphate, and tris(2,4-dichlorophenyl)sulfonium=hexafluorophosphate.

In addition, as a counter anion of the iodonium salt compound and the sulfonium salt compound, a sulfonamide anion or a sulfoneimide anion is preferred, and a sulfoneimide anion is more preferred.

As the sulfonamide anion, an aryl sulfonamide anion is preferred.

In addition, as the sulfoneimide anion, a bisaryl sulfoneimide anion is preferred.

Specific examples of the sulfonamide anion or the sulfoneimide anion will be illustrated below, but the present disclosure is not limited thereto. In the following specific examples, Ph represents a phenyl group, Me represents a methyl group, and Et represents an ethyl group, respectively.

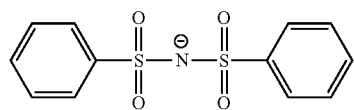

I-1

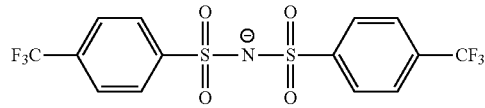

I-2

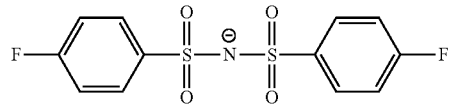

I-3

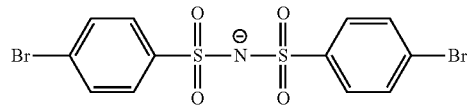

I-4

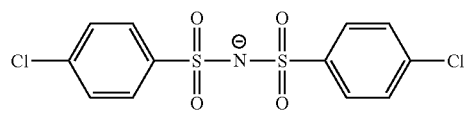

I-5

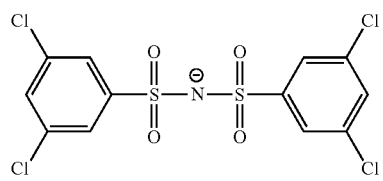

I-6

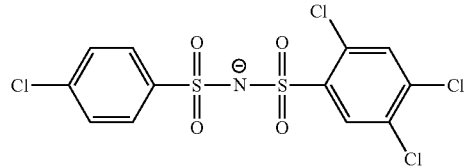

I-7

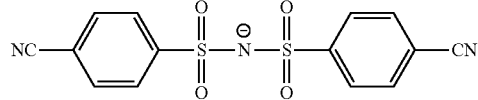

I-8

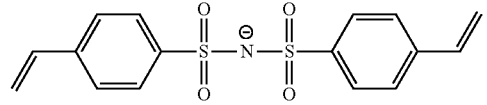

I-9

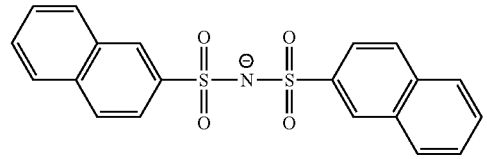

I-10

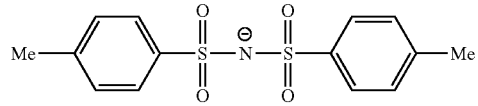

I-11

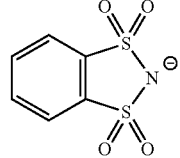

I-12

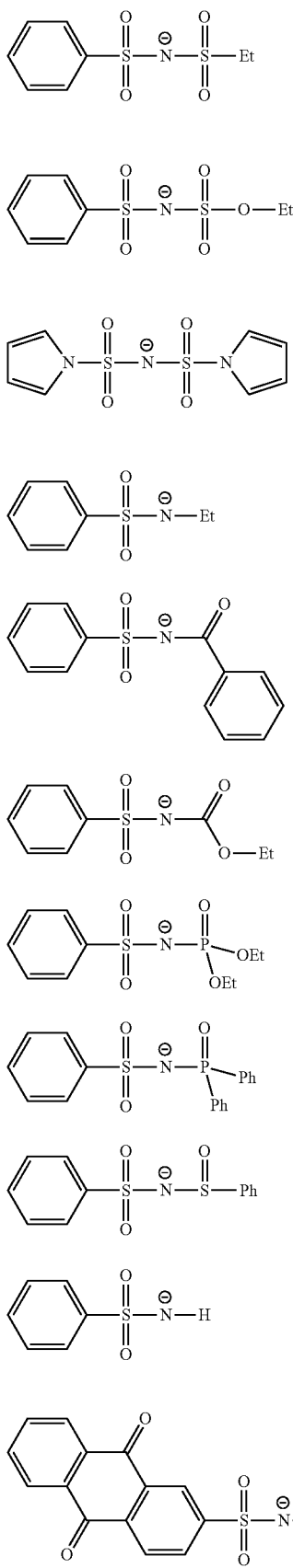

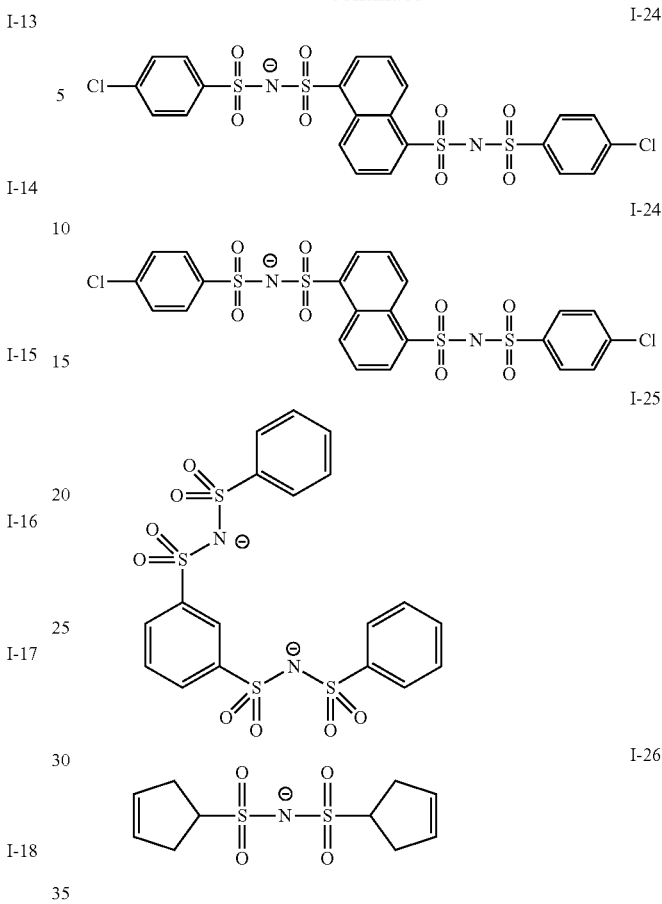

The content of the electron-receiving polymerization initiator is preferably 0.1% by mass to 50% by mass, more preferably 0.5% by mass to 30% by mass, and particularly preferably 0.8% by mass to 20% by mass of the total mass of the image-recording layer.

—Polymer Particle—

The image-recording layer preferably includes a polymer particle.

The polymer particle is preferably selected from the group consisting of a thermoplastic polymer particle, a thermally reactive polymer particle, a polymer particle having a polymerizable group, a microcapsule encapsulating a hydrophobic compound, and a micro gel (crosslinked polymer particle). Among these, a polymer particle having a polymerizable group or a micro gel is preferred. In a particularly preferred embodiment, the polymer particle includes at least one ethylenically unsaturated polymerizable group. Due to the presence of such a polymer particle, an effect for enhancing the printing resistance of the exposed portion and the on-machine developability of the non-exposed portion can be obtained.

In addition, the polymer particle is preferably a thermoplastic polymer particle.

As the thermoplastic polymer particle, thermoplastic polymer particles described in Research Disclosure No. 33303 of January 1992 and the specifications of JP1997-123387A (JP-H09-123387A), JP1997-131850A (JP-H09-131850A), JP1997-171249A (JP-H09-171249A), JP1997-171250A (JP-H09-171250A), EP931647B, and the like are preferred.

Specific examples of a polymer constituting the thermioplastic polymer particle include homopolymers or copolymers of monomers of ethylene, styrene, vinyl chloride, methyl acrylate, ethyl acrylate, methyl methacrylate, ethyl methacrylate, vinylidene chloride, acrylonitrile, vinylcarbazole, acrylates or methacrylates having polyalkylene structures, and the like and mixtures thereof. Preferred examples thereof include copolymers having polystyrene, styrene, and acrylonitrile and polymethyl methacrylate. The average particle diameter of the thermoplastic polymer particle is preferably 0.01 µm to 3.0 µm.

Examples of the thermally reactive polymer particle include a polymer particle having a thermally reactive group. The thermally reactive polymer particle forms a hydrophobilized region through crosslinking by a thermal reaction and a change in a functional group at this time.

The thermally reactive group in the polymer particle having a thermally reactive group may be a functional group that causes any reactions as long as chemical bonds are formed, but is preferably a polymerizable group, and preferred examples thereof include ethylenically unsaturated groups that cause radical polymerization reactions (for example, acryloyl groups, methacryloyl groups, vinyl groups, allyl groups, and the like), cationic polymerizable groups (for example, vinyl groups, vinyloxy groups, epoxy groups, oxetanyl groups, and the like), isocyanato groups that cause addition reactions or blocked bodies thereof, epoxy groups, vinyloxy groups, functional groups having active hydrogen atoms that are reaction partners thereof (for example, amino groups, hydroxy groups, carboxy groups, and the like), carboxy groups that cause condensation reactions, hydroxy groups or amino groups that are reaction partners, acid anhydrides that cause ring-opening addition reactions, amino groups or hydroxy groups which are reaction partners, and the like.

Examples of the microcapsule include microcapsules encapsulating at least part of the constituent components of the image-recording layer as described in JP2001-277740A and JP2001-277742A. The constituent components of the image-recording layer can also be contained outside the microcapsule. A preferred aspect of the image-recording layer containing the microcapsule is a constitution encapsulating the hydrophobic constituent component in the microcapsule and containing the hydrophilic constituent component outside the microcapsule.

The micro gel (crosslinked polymer particle) is capable of containing part of the constituent components of the image-recording layer at least one of on the surface or inside. Particularly, a reactive micro gel having a radical polymerizable group on the surface is preferred from the viewpoint of image-foi wing sensitivity or printing resistance.

In order to encapsulate the constituent components of the image-recording layer in a microcapsule or a microgel, a well-known method can be applied.

In addition, from the viewpoint of printing resistance, contamination resistance, and storage stability, the polymer particle is preferably a polymer particle obtained by a reaction between a polyhydric isocyanate compound that is an adduct of a polyhydric phenol compound having two or more hydroxy groups in the molecule and isophorone diisocyanate and a compound having active hydrogen.

As the polyhydric phenol compound, a compound having a plurality of benzene rings having a phenolic hydroxy group is preferred.

As the compound having active hydrogen, a polyol compound or a polyamine compound is preferred, a polyol compound is more preferred, and at least one compound selected from the group consisting of propylene glycol, glycerin, and trimethylol propane is still more preferred.

As a particle of a resin obtained by a reaction between the polyhydric isocyanate compound that is an adduct of a polyhydric phenol compound having two or more hydroxy groups in the molecule and isophorone diisocyanate and the compound having active hydrogen, a polymer particle described in Paragraphs 0032 to 0095 of JP2012-206495A is preferably exemplified.

Furthermore, from the viewpoint of printing resistance and solvent resistance, the polymer particle preferably has a hydrophobic main chain and includes both i) a constituent unit having a pendant cyano group directly bonding to the hydrophobic main chain and ii) a constituent unit having a pendant group including a hydrophilic polyalkylene oxide segment.

As the hydrophobic main chain, an acrylic resin chain is preferably exemplified.

As an example of the pendant cyano group, —[$CH_2CH(CH_2CH(C\equiv N)$)-] or —[$CH_2C(CH_3)(C\equiv N)$—] is preferably exemplified.

In addition, the constituent unit having the pendant cyano group can be easily derived from an ethylenically unsaturated monomer, for example, acrylonitrile or methacrylonitrile or a combination thereof.

In addition, as an alkylene oxide in the hydrophilic polyalkylene oxide segment, an ethylene oxide or a propylene oxide is preferred, and an ethylene oxide is more preferred.

The number of times of repetition of an alkylene oxide structure in the hydrophilic polyalkylene oxide segment is preferably 10 to 100, more preferably 25 to 75, and still more preferably 40 to 50.

As a particle of a resin having a hydrophobic main chain and including both i) the constituent unit having the pendant cyano group directly bonding to the hydrophobic main chain and ii) the constituent unit having a pendant group including the hydrophilic polyalkylene oxide segment, a particle described in Paragraphs 0039 to 0068 of JP2008-503365A is preferably exemplified.

The average particle diameter of the polymer particle is preferably 0.01 µm to 3.0 µm, more preferably 0.03 µm to 2.0 µm, and still more preferably 0.10 µm to 1.0 µM. In this range, a favorable resolution and favorable temporal stability can be obtained.

The average primary particle diameter of the respective particles in the present disclosure is measured using a light scattering method or by capturing an electron micrograph of a particle, measuring the particle diameters of a total of 5,000 particles on the photograph, and computing the average value. For a non-spherical particle, the particle diameter value of a spherical particle having the same particle area as the particle area on the photograph is regarded as the particle diameter.

In addition, the average particle diameter in the present disclosure is regarded as the volume average particle diameter unless particularly otherwise described.

The content of the polymer particle is preferably 5% by mass to 90% by mass of the total mass of the image-recording layer.

—Polymerizable Compound—

The image-recording layer preferably includes a polymerizable compound.

The polymerizable compound that is used in the present disclosure may be, for example, a radical polymerizable compound or a cationic polymerizable compound, but is preferably an addition polymerizable compound having at least one ethylenically unsaturated bond (ethylenically unsaturated compound). The ethylenically unsaturated compound is preferably a compound having at least one terminal ethylenically unsaturated bond and more preferably a compound having two or more terminal ethylenically unsaturated bonds. The polymerizable compound has a chemical form, for example, a monomer, a prepolymer, that is, a dimer, a trimer, or an oligomer, or a mixture thereof.

Examples of the monomer include unsaturated carboxylic acids (for example, acrylic acid, methacrylic acid, itaconic acid, crotonic acid, isocrotonic acid, maleic acid, and the like), esters thereof, and amides thereof, and esters of unsaturated carboxylic acids and polyhydric amine compounds and amides of unsaturated carboxylic acids and polyhydric alcohol compounds are preferably used. In addition, addition reaction products between unsaturated carboxylic acid esters or amides having a nucleophilic substituent such as a hydroxy group, an amino group, or a mercapto group and monofunctional or polyfunctional isocyanates or epoxies, dehydration condensation reaction products with a monofunctional or polyfunctional carboxylic acid, and the like are also preferably used. In addition, addition reaction products between unsaturated carboxylic acid esters or amides having an electrophilic substituent such as an isocyanate group or an epoxy group and monofunctional or polyfunctional alcohols, amines, or thiols, furthermore, substitution reaction products between unsaturated carboxylic acid esters or amides having a dissociable substituent such as a halogen atom or a tosyloxy groups and monofunctional or polyfunctional alcohols, amines, or thiols are also preferred. In addition, as additional examples, it is also possible to use a group of compounds obtained by substituting the unsaturated carboxylic acid with an unsaturated phosphonic acid, styrene, a vinyl ether, or the like. These compounds are described in JP2006-508380A, JP2002-287344A, JP2008-256850A, JP2001-342222A, JP1997-179296A (JP-H09-179296A), JP1997-179297A (JP-H09-179297A), JP1997-179298A (JP-H09-179298A), JP2004-294935A, JP2006-243493A, JP2002-275129A, JP2003-064130A, JP2003-280187A, JP1998-333321A (JP-H10-333321A), and the like.

As specific examples of monomers of esters of polyhydric alcohol compounds and unsaturated carboxylic acids, examples of acrylic acid esters include ethylene glycol diacrylate, 1,3-butanediol diacrylate, tetramethylene glycol diacrylate, propylene glycol diacrylate, trimethylolpropane triacrylate, hexanediol diacrylate, tetraethylene glycol diacrylate, pentaerythritol tetraacrylate, sorbitol triacrylate, isocyanuric acid ethylene oxide (EO)-modified triacrylate, polyester acrylate oligomers, and the like. Examples of methacrylic acid esters include tetramethylene glycol dimethacrylate, neopentyl glycol dimethacrylate, trimethylolpropane trimethacrylate, ethylene glycol dimethacrylate, pentaerythritol trimethacrylate, bis[p-(3-methacryloxy-2-hydroxypropoxy)phenyl] dimethyl methane, bis[p-(methacryloxyethoxy)phenyl] dimethyl methane, and the like. In addition, specific examples of monomers of amides of polyhydric amine compounds and unsaturated carboxylic acids include methylene bisacrylamide, methylene bismethacrylamide, 1,6-hexamethylene bisacrylamide, 1,6-hexamethylene bismethacrylamide, diethylenetriamine trisacrylamide, xylene bisacrylamide, xylene bismethacrylamide, and the like.

In addition, urethane-based addition polymerizable compounds produced using an addition reaction between an isocyanate and a hydroxy group are also preferred, and specific examples thereof include vinyl urethane compounds having two or more polymerizable vinyl groups in one molecule obtained by adding vinyl monomers having a hydroxy group represented by Formula (M) to a polyisocyanate compound having two or more isocyanate groups in one molecule which is described in, for example, JP1973-041708B (JP-S48-041708B).

$$CH_2=C(R^{M4})COOCH_2CH(R^{M5})OH \quad\quad (M)$$

In Formula (M), $R^{M4}$ and $R^{M5}$ each independently represent a hydrogen atom or a methyl group.

In addition, urethane acrylates described in JP1976-037193A (JP-S51-037193A), JP1990-032293B (JP-H02-032293B), JP1990-016765B (JP-H02-016765B), JP2003-344997A, and JP2006-065210A, urethane compounds having ethylene oxide-based skeletons described in JP1983-049860B (JP-S58-049860B), JP1981-017654B (JP-S56-017654B), JP1987-039417B (JP-S62-039417B), JP1987-039418B (JP-S62-039418B), JP2000-250211A, and JP2007-094138A, and urethane compounds having hydrophilic groups described in U.S. Pat. No. 7,153,632B, JP1996-505958A (JP-H08-505958A), JP2007-293221A, and JP2007-293223A are also preferred.

The details of the structure of the polymerizable compound and a method for using the polymerizable compound such as whether to be used singly or jointly or the amount added can be randomly set.

The content of the polymerizable compound is preferably 5% by mass to 75% by mass, more preferably 10% by mass to 70% by mass, and particularly preferably 15% by mass to 60% by mass of the total mass of the image-recording layer.

—Binder Polymer—

The image-recording layer preferably includes a binder polymer.

The binder polymer is preferably a (meth)acrylic resin, a polyvinyl acetal resin, or a polyurethane resin.

Among these, as the binder polymer, it is possible to preferably use well-known binder polymers that can be used in the image-recording layer in the lithographic printing plate precursor. As an example, a binder polymer that is used for an on-machine development-type lithographic printing plate precursor (hereinafter, also referred to as the binder polymer for on-machine development) will be described in detail.

As the binder polymer for on-machine development, a binder polymer having an alkylene oxide chain is preferred. The binder polymer having an alkylene oxide chain may have a poly(alkylene oxide) portion in a main chain or in a side chain. In addition, the binder polymer may be a graft polymer having poly(alkylene oxide) in a side chain or a block copolymer of a block constituted of a poly(alkylene oxide)-containing repeating unit and a block constituted of an (alkylene oxide)-non-containing repeating unit.

In the case of having a poly(alkylene oxide) portion in the main chain, the binder polymer is preferably a polyurethane resin. As a polymer in the main chain in a case in which the binder polymer has a poly(alkylene oxide) portion in the side chain, a (meth)acrylic resin, a polyvinyl acetal resin, a polyurethane resin, a polyurea resin, a polyimide resin, a polyamide resin, an epoxy resin, a polystyrene resin, a novolac-type phenol resin, a polyester resin, synthetic rubber, and natural rubber are exemplified, and, particularly, a (meth)acrylic resin is preferred.

In addition, as another preferred example of the binder polymer, a polymer compound which has a polyfunctional (hexafunctional to decafunctional) thiol as a nucleus and has polymer chains bonding to this nucleus through sulfide bonds and in which the polymer chain has a polymerizable group (hereinafter, also referred to as the star-shaped polymer compound) is exemplified. As the star-shaped polymer compound, for example, a compound described in JP2012-148555A can be preferably used.

As the star-shaped polymer compound, a star-shaped polymer compound having a polymerizable group such as an ethylenically unsaturated bond for improving the film hardness of the image area in a main chain or a side chain, preferably, in a side chain as described in JP2008-195018A is exemplified. The polymerizable group forms a crosslink between polymer molecules, and curing is accelerated.

As the polymerizable group, an ethylenically unsaturated group such as a (meth)acrylic group, a vinyl group, an allyl group, or a styryl group, an epoxy group, or the like is preferred, a (meth)acrylic group, a vinyl group, and a styryl group are more preferred from the viewpoint of a polymerization reaction property, and a (meth)acrylic group is particularly preferred. These groups can be introduced to the polymer by a polymer reaction or copolymerization. For example, it is possible to use a reaction between a polymer having a carboxy group in a side chain and glycidyl methacrylate or a reaction between a polymer having an epoxy group and an ethylenically unsaturated group-containing carboxylic acid such as methacrylic acid. These groups may be jointly used.

Regarding the molecular weight of the binder polymer, the weight-average molecular weight (Mw) as a polystyrene equivalent value by a GPC method is preferably 2,000 or more, more preferably 5,000 or more, and still more preferably 10,000 to 300,000.

If necessary, it is possible to jointly use a hydrophilic polymer such as polyacrylic acid or polyvinyl alcohol described in JP2008-195018A. In addition, it is also possible to jointly use a lipophilic polymer and a hydrophilic polymer.

In the image-recording layer that is used in the present disclosure, the binder polymer may be used singly or two or more binder polymers may be jointly used.

The binder polymer can be added to the image-recording layer in a random amount, but the content of the binder polymer is preferably 1% by mass to 90% by mass and more preferably 5% by mass to 80% by mass of the total mass of the image-recording layer.

—Acid Color Developing Agent—

The image-recording layer preferably includes an acid color developing agent other than the specific dye compound (hereinafter, simply referred to as the "acid color developing agent").

The "acid color developing agent" that is used in the present disclosure refers to a compound having a property of developing color by being heated in a state of receiving an electron-receiving compound (for example, a proton such as an acid). The acid color developing agent is particularly preferably a colorless compound which has a partial skeleton such as lactone, lactam, sultone, spiropyran, an ester, or an amide and in which the partial skeleton rapidly ring-opens or cleavages in the case of coming into contact with the electron-receiving compound.

Examples of the above-described acid color developing agent include phthalides such as 3,3-bis(4-dimethylaminophenyl)-6-dimethylaminophthalide (referred to as "crystal violet lactone"), 3,3-bis(4-dimethylaminophenyl)phthalide, 3-(4-dimethylaminophenyl)-3-(4-diethylamino-2-methylphenyl)-6-dimethylaminophthalide, 3-(4-dimethylaminophenyl)-3-(1,2-dimethylindol-3-yl)phthalide, 3-(4-dimethylaminophenyl)-3-(2-methylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazole-3-yl)-6-dimethylaminophthalide, 3,3-bis(2-phenylindol-3-yl)-6-dimethylaminophthalide, 3-(4-dimethylaminophenyl)-3-(1-methylpyrrole-3-yl)-6-dimethylaminophthalide, 3,3-bis[1,1-bis(4-dimethylaminophenyl)ethylene-2-yl]-4,5,6,7-tetrachlorophthalide, 3,3-bis[1,1-bis(4-pyrrolidinophenyl)ethylene-2-yl]-4,5,6,7-tetrabromophthalide, 3,3-bis[1-(4-dimethylaminophenyl)-1-(4-methoxyphenyl)ethylene-2-yl]-4,5,6,7-tetrachlorophthalide, 3,3-bis[1-(4-pyrrolidinophenyl)-1-(4-methoxyphenyl)ethylene-2-yl]-4,5,6,7-tetrachlorophthalide, 3-[1,1-di(1-ethyl-2-methylindol-3-yl)ethylene-2-yl]-3-(4-diethylaminophenyl)phthalide, 3-[1,1-di(1-ethyl-2-methylindol-3-yl)ethylene-2-yl]-3-(4-N-ethyl-N-phenylaminophenyl)phthalide, 3-(2-ethoxy-4-diethylaminophenyl)-3-(1-n-octyl-2-methylindol-3-yl)-phthalide, 3,3-bis(1-n-octyl-2-methylindol-3-yl)-phthalide, and 3-(2-methyl-4-diethylaminophenyl)-3-(1-n-octyl-2-methylindol-3-yl)-phthalide, fluoranthenes such as 4,4-bis-dimethylaminobenzhydryl benzyl ether, N-halophenyl-leucoauramine, N-2,4,5-trichlorophenyl leucoauramine, rhodamine-B-anilinolactam, rhodamine-(4-nitroanilino) lactam, rhodamine-B-(4-chloroanilino) lactam, 3,7-bis(diethylamino)-10-benzoylphenoxazine, benzoyl leuco methylene blue, 4-nitrobenzoylmethylene blue, 3,6-dimethoxyfluoran, 3-dimethylamino-7-methoxyfluoran, 3-diethylamino-6-methoxyfluoran, 3-diethylamino-7-methoxyfluoran, 3-diethylamino-7-chlorofluoran, 3-diethylamino-6-methyl-7-chlorofluoran, 3-diethylamino-6,7-dimethylfluoran, 3-N-cyclohexyl-N-n-butylamino-7-methylfluoran, 3-diethylamino-7-dibenzylaminofluoran, 3-diethylamino-7-octylaminofluoran, 3-diethylamino-7-di-n-hexylaminofluoran, 3-diethylamino-7-anilinofluoran, 3-diethylamino-7-(2'-fluorophenylamino)fluoran, 3-diethylamino-7-(2'-chlorophenylamino)fluoran, 3-diethylamino-7-(3'-chlorophenylamino)fluoran, 3-diethylamino-7-(2',3'-dichlorophenylamino)fluoran, 3-diethylamino-7-(3'-trifluoromethylphenylamino)fluorane, 3-di-n-butylamino-7-(2'-fluorophenylamino)fluoran, 3-di-n-butylamino-7-(2'-chlorophenylamino)fluoran, 3-N-isopentyl-N-ethylamino-7-(2'-chlorophenylamino)fluorane, 3-N-n-hexyl-N-ethylamino-7-(2'-chlorophenylamino) fluoran, 3-diethylamino-6-chloro-7-anilinolluoran, 3-di-n-butylamino-6-chloro-7-anilinofluoran, 3-diethylamino-6-methoxy-7-anilinofluoran, 3-di-n-butylamino-6-ethoxy-7-anilinofluoran, 3-pyrrolidino-6-methyl-7-anilinofluoran, 3-piperidino-6-methyl-7-anilinofluoran, 3-morpholino-6-methyl-7-anilinofluoran, 3-dimethylamino-6-methyl-7-anilinofluoran, 3-diethylamino-6-methyl-7-anilinofluoran, 3-di-n-butylamino-6-methyl-7-anilinaluoran, 3-di-n-pentylamino-6-methyl-7-anilinofluoran, 3-N-ethyl-N-methylamino-6-methyl-7-anilinofluoran, 3-N-n-propyl-N-methylamino-6-methyl-7-anilinofluoran, 3-N-n-propyl-N-ethylamino-6-methyl-7-anilinofluoran, 3-N-n-butyl-N-methylamino-6-methyl-7-anilinofluoran, 3-N-n-butyl-N-ethylamino-6-methyl-7-anilinofluoran, 3-N-isobutyl-N-ethylamino-6-methyl-7-anilinofluoran, 3-N-isobutyl-N-ethylamino-6-methyl-7-anilinofluoran, 3-N-isopentyl-N-ethylamino-6-methyl-7-anilinofluoran, 3-N-n-hexyl-N-methylamino-6-methyl-7-anilinofluoran, 3-N-cyclohexyl-N-ethylamino-6-methyl-7-anilinofluoran, 3-N-cyclohexyl-N-n-propylamino-6-methyl-7-anilinofluoran, 3-N-cyclohexyl-N-n-butylamino-6-methyl-7-anilinofluoran, 3-N-cyclohexyl-N-n-hexylamino-6-methyl-7-anilinofluoran, 3-N-cyclohexyl-N-n-octylamino-6-methyl-7-anilinofluoran, 3-N-(2'-methoxyethyl)-N-methylamino-6-methyl-7-anilinofluoran, 3-N-(2'-methoxyethyl)-N-ethylamino-6-methyl-7-anilinofluoran, 3-N-(2'-methoxyethyl)-N-isobutylamino-6-methyl-7-anilinofluoran, 3-N-(2'-ethoxyethyl)-N-methylamino-6-methyl-7-anilinofluoran, 3-N-(2'-ethoxyethyl)-N-ethylamino-6-methyl-7-anilinofluoran, 3-N-(3'-methoxypropyl)-N-methylamino-6-methyl-7-anilinofluoran, 3-N-(3'-methoxypropyl)-N-ethylamino-6-methyl-7-anilinofluoran, 3-N-(3'-ethoxypropyl)-N-ethylamino-6-methyl-7-anilinofluoran, 3-N-(3'-ethoxypropyl)-N-methylamino-6-methyl-7-anilinofluoran, 3-N-(2'-tetrahydrofurfuryl)-N-ethylamino-6-methyl-7-anilinofluoran, 3-N-(4'-methylphenyl)-N-ethylamino-6-methyl-7-anilinofluoran, 3-diethylamino-6-methyl-7-anilinofluran, 3-diethylamino-6-methyl-7-(3'-methylphenylamino)fluoran, 3-diethylamino-6-methyl-7-(2',6'-methylphenylamino)fluoran, 3-di-n-butylamino-6-methyl-7-(2',6'-methylphenylamino)fluoran, 3-di-n-butylamino-7-(2',6'-dimethylphenylamino)fluoran, 2,2-bis[4'-(3-N-cyclohexyl-N-methylamino-6-methylfluoran)-7-ylaminophenyl]propane, 3-[4'-(4-phenylaminophenyl)aminophenyl] amino-6-methyl-7-chlorofluoran, and 3-[4'-(dimethylaminophenyl)] amino-5,7-dimethylfluoran, phthalides such as 3-(2-methyl-4-diethylaminophenyl)-3-(1-ethyl-2-methylindol-3-yl)-4-azaphthalide, 3-(2-n-propoxycarbonylamino-4-di-n-propylaminophenyl)-3-(1-ethyl-2-methylindol-3-yl)-4-a zaphthalide, 3-(2-methylamino-4-di-n-propylaminophenyl)-3-(1-ethyl-2-methylindol-3-yl)-4-azaphthalide, 3-(2-methyl-4-di n-hexylaminophenyl)-3-(1-n-octyl-2-methylindol-3-yl)-4,7-diazaphthalide, 3,3-bis(2-ethoxy-4-diethylaminophenyl)-4-azaphthalide, 3,3-bis(1-n-octyl-2-methylindol-3-yl)-4-azaphthalide, 3-(2-ethoxy-4-diethylaminophenyl)-3-(1-ethyl-2-methylindol-3-yl)-4-azaphthalide, 3-(2-ethoxy-4-diethylaminophenyl)-3-(1-octyl-2-methylindol-3-yl)-4 or 7-azaphthalide, 3-(2-ethoxy-4-diethylaminophenyl)-3-(1-ethyl-2-methylindol-3-yl)-4 or 7-azaphthalide, 3-(2-hexyloxy-4-diethylaminophenyl)-3-(1-ethyl-2-methylindol-3-yl)-4 or 7-azaphthalide, 3-(2-ethoxy-4-diethylaminophenyl)-3-(1-ethyl-2-phenylindol-3-yl)-4 or 7-azaphthalide, 3-(2-butoxy-4-diethylaminophenyl)-3-(1-ethyl-2-phenylindol-3-yl)-4 or 7-azaphthalide, 3-methyl-spiro-dinaphthopyran, 3-ethyl-spiro-dinaphthopyran, 3-phenyl-spiro-dinaphthopyran, 3-benzyl-spiro-dinaphthopyran, 3-methyl-naphtho-(3-methoxybenzo)spiropyran, 3-propyl-spiro-dibenzopyran-3,6-bis(dimethylamino)fluorene-9-spiro-3'-(6'-dimethylamino)phthalide, and 3,6-bis(diethylamino)fluorene-9-spiro-3'-(6'-dimethylamino)phthalide, additionally, 2'-anilino-6'-(N-ethyl-N-isopentyl) amino-3'-methylspiro[isobenzofuran-(3H), 9'-(9H) xanthene]-3-one, 2'-anilino-6'-(N-ethyl-N-(4-methylphenyl))amino-3'-methylspiro[isobenzofuran-1 (3H), 9'-(9H) xanthene]-3-one, 3'-N,N-dibenzylamino-6'-N,N-diethylaminospiro[isobenzofuran-1 (3H), 9'-(9H) xanthene]-3-one, 2'-(N-methyl-N-phenyl)amino-6'-(N-ethyl-N-(4-methylphenyl))aminospiro[isobenzofuran-1 (3H), xanthene]-3-one, and the like.

Among these, from the viewpoint of color developability, the acid color developing agent that is used in the present disclosure is preferably at least one compound selected from the group consisting of a spiropyran compound, a spirooxazine compound, a spirolactone compound, or a spirolactam compound.

The hue of the colorant after color development is preferably green, blue, or black from the viewpoint of visibility.

As the acid color developing agent, it is also possible to use commercially available products, and examples thereof include ETAC, RED 500, RED 520, CVL, S-205, BLACK 305, BLACK 400, BLACK 100, BLACK 500, H-7001, GREEN 300, NIRBLACK 78, BLUE 220, H-3035, BLUE 203, ATP, H-1046, H-2114 (all manufactured by Fukui Yamada Chemical Co., Ltd.), ORANGE-DCF, Vermilion-DCF, PINK-DCF, RED-DCF, BLMB, CVL, GREEN-DCF, TH-107 (all manufactured by Hodogaya Chemical Co., Ltd.), ODB, ODB-2, ODB-4, ODB-250, ODB-Black XV, Blue-63, Blue-502, GN-169, GN-2, Green-118, Red-40, Red-8 (all manufactured by Yamamoto Chemicals Inc.), crystal violet lactone (manufactured by Tokyo Chemical Industry Co., Ltd.), and the like. Among these commercially available products, ETAC, S-205, BLACK 305, BLACK 400, BLACK 100, BLACK 500, H-7001, GREEN 300, NIRBLACK 78, H-3035, ATP, H-1046, H-2114, GREEN-DCF, Blue-63, GN-169, and crystal violet lactone are preferred since the visible light absorbance of films to be formed is favorable.

These acid color developing agents may be used singly, or two or more components can also be used in combination.

The content of the acid color developing agent is preferably 0.5% by mass to 10% by mass and more preferably 1% by mass to 5% by mass of the total mass of the image-recording layer.

—Chain Transfer Agent—

The image-recording layer that is used in the present disclosure may contain a chain transfer agent. The chain transfer agent contributes to the improvement of the printing resistance in lithographic printing plates.

The chain transfer agent is preferably a thiol compound, more preferably a thiol having 7 or more carbon atoms from the viewpoint of the boiling point (difficulty of being volatilized), and still more preferably a compound having a mercapto group on an aromatic ring (aromatic thiol compound). The thiol compound is preferably a monofunctional thiol compound.

Specific examples of the chain transfer agent include the following compounds.

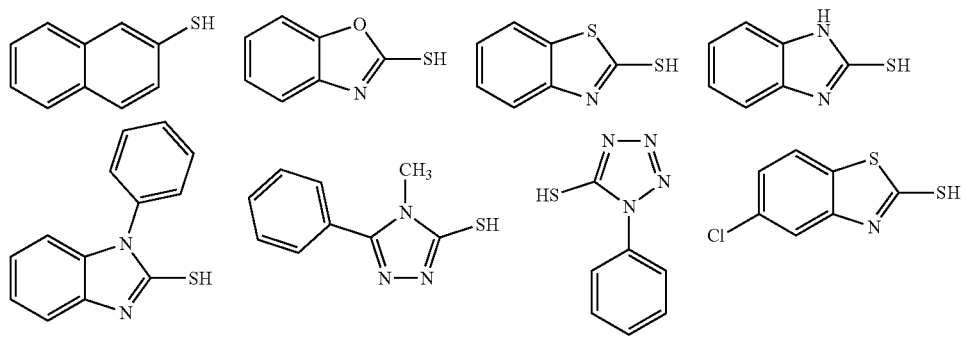

-continued
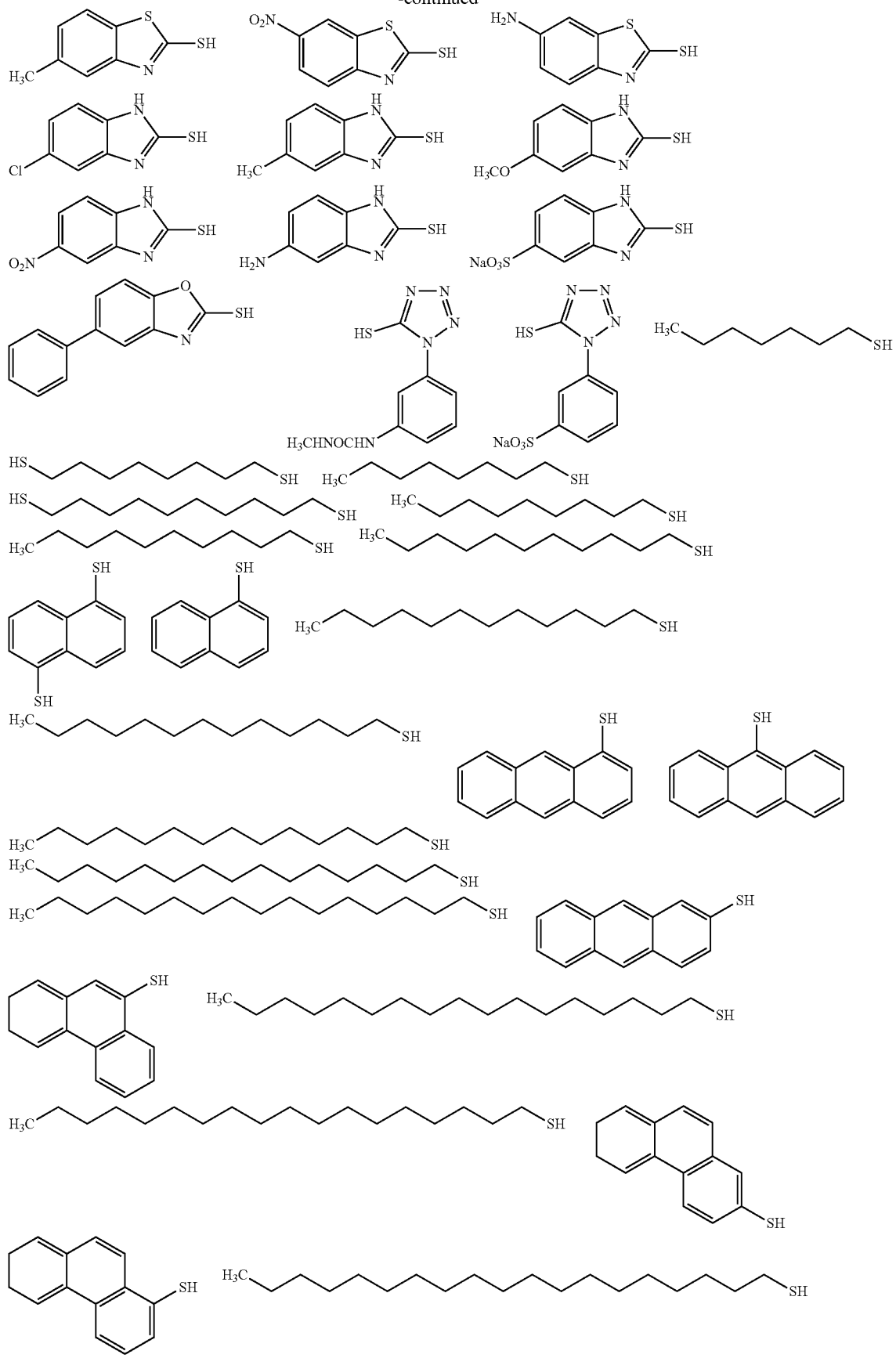

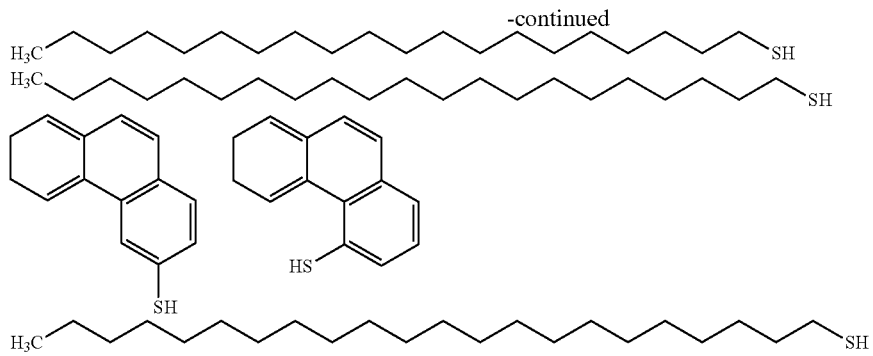

Only one chain transfer agent may be added or two or more chain transfer agents may be jointly used.

The content of the chain transfer agent is preferably 0.01% by mass to 50% by mass, more preferably 0.05% by mass to 40% by mass, and still more preferably 0.1% by mass to 30% by mass of the total mass of the image-recording layer.

—Low-Molecular-Weight Hydrophilic Compound—

In order to improve the on-machine developability while suppressing the degradation of printing resistance, the image-recording layer may contain a low-molecular-weight hydrophilic compound. The low-molecular-weight hydrophilic compound is preferably a compound having a molecular weight of smaller than 1,000, more preferably a compound having a molecular weight of smaller than 800, and still more preferably a compound having a molecular weight of smaller than 500.

As the low-molecular-weight hydrophilic compound, examples of water-soluble organic compounds include glycols such as ethylene glycol, diethylene glycol, triethylene glycol, propylene glycol, dipropylene glycol, and tripropylene glycol and ethers or ester derivative thereof, polyols such as glycerin, pentaerythritol, and tris(2-hydroxyethyl) isocyanurate, organic amines such as triethanolamine, diethanolamine, and monoethanolamine and salts thereof, organic sulfonic acids such as alkyl sulfonic acid, toluenesulfonic acid, and benzenesulfonic acid and salts thereof, organic sulfamic acids such as alkyl sulfamate and salts thereof, organic sulfuric acids such as alkyl sulfates and alkyl ether sulfates and salts thereof, organic phosphonic acids such as phenylphosphonic acid and salts thereof, organic carboxylic acids such as tartaric acid, oxalic acid, citric acid, malic acid, lactic acid, gluconic acid, and amino acid and salts thereof, betaines, and the like.

As the low-molecular-weight hydrophilic compound, at least one selected from polyols, organic sulfates, organic sulfonates, or betaines is preferably contained.

Specific examples of the organic sulfonates include alkyl sulfonates such as sodium n-butyl sulfonate, sodium n-hexyl sulfonate, sodium 2-ethylhexyl sulfonate, sodium cyclohexyl sulfonate, and sodium n-octyl sulfonate; alkyl sulfonates having ethylene oxide chains such as sodium 5,8,11-trioxapentadecane-1-sulfonate, sodium 5,8,11-trioxaheptadecane-1-sulfonate, sodium 13-ethyl-5,8,11-trioxaheptadecane-1-sulfonate, sodium 5,8,11,14-tetraoxatetracosane-1-sulfonate; aryl sulfonates such as sodium benzene sulfonate, sodium p-toluenesulfonate, sodium p-hydroxybenzene sulfonate, sodium p-styrene sulfonate, sodium dimethyl isophthalate-5-sulfonate, sodium 1-naphthyl sulfonate, sodium 4-hydroxynaphthylsulfonate, sodium 1,5-naphthalene disulfonate, and trisodium 1,3,6-naphthalene trisulfonate; compounds described in Paragraphs 0026 to 0031 of JP2007-276454A and Paragraphs 0020 to 0047 of JP2009-154525A; and the like. The salts may be potassium salts or lithium salts.

Examples of the organic sulfates include sulfates of alkyls, alkenyls, alkynyls, aryls, or heterocyclic monoethers of polyethylene oxides. The number of ethylene oxide units is preferably in a range of 1 to 4, and the salts are preferably sodium salts, potassium salts, or lithium salts. Specific examples thereof include compounds described in Paragraphs 0034 to 0038 of JP2007-276454A.

The betaines are preferably compounds in which the number of carbon atoms in hydrocarbon substituents into nitrogen atoms is in a range of 1 to 5, and specific examples thereof include trimethyl ammonium acetate, dimethyl propyl ammonium acetate, 3-hydroxy-4-trimethyl ammonio butyrate, 4-(1-pyridinio) butyrate, 1-hydroxyethyl-1-imidazolio acetate, trimethyl ammonium methanesulfonate, dimethyl propyl ammonium methanesulfonate, 3-trimethylammonio-1-propane sulfonate, 3-(1-pyridinio)-1-propane sulfonate, and the like.

Since the low-molecular-weight hydrophilic compound has a small structure in hydrophobic portions and barely has surfactant actions, there are no cases in which dampening water permeates exposed portions (image areas) in the image-recording layer and thus the hydrophobic properties or membrane hardness of the image areas degrade, and it is possible to favorably maintain the ink-receiving properties or printing resistance of the image-recording layer.

The content of the low-molecular-weight hydrophilic compound is preferably in a range of 0.5% by mass to 20% by mass, more preferably in a range of 1% by mass to 15% by mass, and still more preferably in a range of 2% by mass to 10% by mass of the total mass of the image-recording layer. In a case in which the content is in this range, favorable on-machine developability and favorable printing resistance can be obtained.

The low-molecular-weight hydrophilic compound may be used singly or two or more low-molecular-weight hydrophilic compounds may be used in a mixture form.

—Sensitization Agent—

In order to improve the ink-absorbing property, the image-recording layer may contain a sensitization agent such as a phosphonium compound, a nitrogen-containing low-molecular-weight compound, or an ammonium group-containing polymer. Particularly, in a case in which an inorganic lamellar compound is contained in the protective layer, these compounds function as surface coating agents for the inorganic lamellar compound and are capable of suppressing the ink-absorbing properties from being degraded in the middle of printing due to the inorganic lamellar compound.

Among these, a phosphonium compound, a nitrogen-containing low-molecular-weight compound, and an ammonium group-containing polymer are preferably jointly used as the sensitization agent, and a phosphonium compound, quaternary ammonium salts, and an ammonium group-containing polymer are more preferably jointly used.

Examples of a phosphonium compound include phosphonium compounds described in JP2006-297907A and JP2007-050660A. Specific examples thereof include tetrabutylphosphonium iodide, butyltriphenylphosphonium bromide, tetraphenylphosphonium bromide, 1,4-bis(triphenylphosphonio)butane=di(hexafluorophosphate), 1,7-bis(triphenylphosphonio)heptane=sulfate, 1,9-bis(triphenylphosphonio)nonane=naphthalene-2,7-disulfonate, and the like.

Examples of the nitrogen-containing low-molecular-weight compound include amine salts and quaternary ammonium salts. In addition, examples thereof include imidazolinium salts, benzo imidazolinium salts, pyridinium salts, and quinolinium salts. Among these, quaternary ammonium salts and pyridinium salts are preferred. Specific examples thereof include tetramethylammonium=hexafluorophosphate, tetrabutylammonium=hexafluorophosphate, dodecyltrimethylammonium=p-toluene sulfonate, benzyltriethylammonium=hexafluorophosphate, benzyldimethyloctylammonium=hexafluorophosphate, benzyldimethyldodecylammonium=hexafluorophosphate, compounds described in Paragraphs 0021 to 0037 of JP2008-284858A and Paragraphs 0030 to 0057 of JP2009-090645A, and the like.

The ammonium group-containing polymer needs to have an ammonium group in the structure, and polymers including 5% by mol to 80% by mol of (meth)acrylate having ammonium groups in side chains as copolymerization components are preferred. Specific examples thereof include polymers described in Paragraphs 0089 to 0105 of JP2009-208458A.

In the ammonium salt-containing polymer, the value of the reducing specific viscosity (unit: ml/g) obtained according to the measurement method described in JP2009-208458A is preferably in a range of 5 to 120, more preferably in a range of 10 to 110, and particularly preferably in a range of 15 to 100. In a case in which the reducing specific viscosity is converted to the weight-average molecular weight (Mw), the weight-average molecular weight is preferably in a range of 10,000 to 150,000, more preferably in a range of 17,000 to 140,000, and particularly preferably in a range of 20,000 to 130,000.

Hereinafter, specific examples of the ammonium group-containing polymer will be described.

(1) 2-(Trim ethyl ammonio)ethyl methacrylate=p-toluenesulfonate/3,6-dioxaheptyl methacrylate copolymer (molar ratio: 10/90, Mw: 45,000)

(2) 2-(Trimethylammonio)ethyl methacrylate=hexafluorophosphate/3,6-dioxaheptyl methacrylate copolymer (molar ratio: 20/80, Mw: 60,000)

(3) 2-(Ethyldimethylammonio)ethyl methacrylate=p-toluenesulfonate/hexyl methacrylate copolymer (molar ratio: 30/70, Mw: 45,000)

(4) 2-(Trimethylammonio)ethyl methacrylate=hexafluorophosphate/2-ethylhexyl methacrylate copolymer (molar ratio: 20/80, Mw: 60,000)

(5) 2-(Trimethylammonio)ethyl methacrylate=methylsulfate/hexyl methacrylate copolymer (molar ratio: 40/60, Mw: 70,000)

(6) 2-(Butyldimethylammonio)ethyl methacrylate=hexafluorophosphate/3,6-dioxaheptyl methacrylate copolymer (molar ratio: 25/75, Mw: 65,000)

(7) 2-(Butyldimethylammonio)ethyl acrylate=haxafluorophosphate/3,6-dioxaheptyl methacrylate copolymer (molar ratio: 20/80, Mw: 65,000)

(8) 2-(Butyldimethylammonio)ethyl methacrylate=13-ethyl-5,8,11-trioxa-1-heptadecanesulfonate/3,6-dioxaheptyl methacrylate copolymer (molar ratio: 20/80, Mw: 75,000)

(9) 2-(Butyldimethylammonio)ethyl methacrylate=haxafluorophosphate/3,6-dioxaheptyl methacrylate/2-hydroxy-3-methacryloyloxypropyl methacrylate copolymer (molar ratio: 15/80/5, Mw: 65,000)

The content of the sensitization agent is preferably in a range of 0.01% by mass to 30.0% by mass, more preferably in a range of 0.1% by mass to 15.0% by mass, and still more preferably in a range of 1% by mass to 10% by mass of the total mass of the image-recording layer.

—Other Components—

To the image-recording layer, it is possible to add, as other components, a surfactant, a polymerization inhibitor, a higher-fatty acid derivative, a plasticizer, inorganic particles, an inorganic lamellar compound, or the like. Specifically, the composition may contain individual components described in Paragraphs 0114 to 0159 of JP2008-284817A.

—Formation of Image-Recording Layer—

The image-recording layer in the lithographic printing plate precursor according to the embodiment of the present disclosure can be formed by, for example, as described in Paragraphs 0142 and 0143 of JP2008-195018A, preparing a coating fluid by dispersing or dissolving the respective necessary components described above in a well-known solvent, applying the coating fluid onto a support using a well-known method such as bar coater coating, and drying the coating fluid. The coating amount (solid content) of the image-recording layer applied after application and drying varies depending on applications; however, is preferably 0.3 g/m$^2$ to 3.0 g/m$^2$. Within this range, a favorable sensitivity and favorable membrane characteristics of the image-recording layer can be obtained.

As the solvent, a well-known solvent can be used. Specific examples thereof include water, acetone, methyl ethyl ketone (2-butanone), cyclohexane, ethyl acetate, ethylene dichloride, tetrahydrofuran, toluene, ethylene glycol monomethyl ether, ethylene glycol monoethyl ether, ethylene glycol dimethyl ether, propylene glycol monomethyl ether, propylene glycol monoethyl ether, acetylacetone, cyclohexanone, diacetone alcohol, ethylene glycol monomethyl ether acetate, ethylene glycol ethyl ether acetate, ethylene glycol monoisopropyl ether, ethylene glycol monobutyl ether acetate, 1-methoxy-2-propanol, 3-methoxy-1-propanol, methoxy methoxyethanol, diethylene glycol monomethyl ether, diethylene glycol monoethyl ether, diethylene glycol dimethyl ether, diethylene glycol diethyl ether, propylene glycol monomethyl ether acetate, propylene glycol monoethyl ether acetate, 3-methoxypropyl acetate, N,N-dimethylfonnamide, dimethyl sulfoxide, γ-butyrolactone, methyl lactate, ethyl lactate, and the like. The solvent may be used singly or two or more solvents may be jointly used. The concentration of the solid content in the coating fluid is preferably approximately 1% to 50% by mass.

The coating amount (solid content) of the image-recording layer after application and drying varies depending on applications; however, is preferably approximately 0.3 to 3.0 g/m² from the viewpoint of obtaining a favorable sensitivity and favorable membrane characteristics of the image-recording layer.

<Support>

The support in the lithographic printing plate precursor according to the embodiment of the present disclosure can be appropriately selected from well-known hydrophilic supports for a lithographic printing plate precursor and used. As the support, a hydrophilic support is preferably exemplified. The hydrophilic support is preferably an aluminum plate which has been roughened using a well-known method and anodized.

On the aluminum plate, as necessary, enlargement processes or sealing processes of micropores in anodized films described in JP2001-253181A and JP2001-322365A, surface hydrophilization processes using alkali metal silicate as described in the specifications of US2,714,066A, US3,181, 461A, US3,280,734A, and US3,902,734A, and surface hydrophilization processes using polyvinyl phosphate or the like as described in the specifications of US3,276,868A, US4,153,461A, and US4,689,272A may be appropriately selected and carried out.

In the support, the center line average roughness is preferably in a range of 0.10 μm to 1.2 μm.

The support may have, as necessary, a backcoat layer including an organic polymer compound described in JP1993-045885A (JP-H05-045885A) or an alkoxy compound of silicon described in JP1994-035174A (JP-H06-035174A) on the surface opposite to the image-recording layer.

<Undercoat Layer>

The lithographic printing plate precursor according to the embodiment of the disclosure preferably has an undercoat layer (in some cases, referred to as the interlayer) between the image-recording layer and the support. The undercoat layer strengthens adhesiveness between the support and the image-recording layer in exposed portions and facilitates peeling the support and the image-recording layer in non-exposed portions, and thus the undercoat layer contributes to improving developability without impairing printing resistance. In addition, in the case of exposure using infrared lasers, the undercoat layer functions as an adiabatic layer and thus has an effect of preventing the sensitivity from being degraded due to the diffusion of heat generated by exposure in the support.

Examples of compounds that can be used for the undercoat layer include polymers having adsorbent groups that can be adsorbed to the surface of the support and hydrophilic groups. In order to improve adhesiveness to the image-recording layer, polymers having adsorbent groups and hydrophilic groups and further having crosslinking groups are preferred. The compounds that can be used for the undercoat layer may be low-molecular-weight compounds or polymers. The compounds that can be used for the undercoat layer may be used in a mixed form of two or more kinds as necessary.

In a case in which the compounds that are used for the undercoat layer are polymers, copolymers of monomers having adsorbent groups, monomers having hydrophilic groups, and monomers having crosslinking groups are preferred.

The adsorbent groups that can be adsorbed to the surface of the support are preferably phenolic hydroxy groups, carboxy groups, —PO₃H₂, —OPO₃H₂, —CONHSO₂—, —SO₂NHSO₂—, —COCH₂COCH₃. The hydrophilic groups are preferably sulfo groups or salts thereof and salts of carboxy groups. The crosslinking groups are preferably acrylic groups, methacryl groups, acrylamide groups, methacrylamide groups, allyl groups, and the like.

The polymers may have crosslinking groups introduced due to the formation of salts between polar substituents of the polymers and compounds having substituents having the polar substituents and opposite charges of the above-described polar substituents and ethylenically unsaturated bonds and may be further copolymerized with monomers other than the above-described monomers, preferably, hydrophilic monomers.

Specifically, preferred examples thereof include silane coupling agents having ethylenic double bond reactive groups that are capable of addition polymerization described in JP1998-282679A (JP-H10-282679A) and phosphorus compounds having ethylenic double bond reactive groups described in JP1990-304441A (JP-H02-304441A).

Low-molecular-weight or high-molecular-weight compounds having crosslinking groups (preferably ethylenically unsaturated bond groups), functional groups that interact with the surface of the support, and hydrophilic groups described in JP2005-238816A, JP2005-125749A, JP2006-239867A, and JP2006-215263A are also preferably used.

More preferred examples thereof include high-molecular-weight polymers having adsorbent groups that can be adsorbed to the surface of the support, hydrophilic groups, and crosslinking groups described in JP2005-125749A and JP2006-188038A.

The content of ethylenically unsaturated bond groups in the polymer that is used in the undercoat layer is preferably in a range of 0.1 mmol to 10.0 mmol and more preferably in a range of 0.2 mmol to 5.5 mmol per gram of the polymer.

The weight-average molecular weight (Mw) of the polymer that is used in the undercoat layer is preferably 5,000 or higher and more preferably in a range of 10,000 to 300,000.

In addition to the above-described compounds for the undercoat layer, the undercoat layer may also include a chelating agent, secondary or tertiary amines, a polymerization inhibitor, compounds having amino groups or functional groups having a polymerization-inhibiting function and groups that interact with the surfaces of supports (for example, 1,4-diazabicyclo[2.2.2]octane (DABCO), 2,3,5,6-tetrahydroxy-p-quinone, chloranil, sulfophthalic acid, hydroxyethyl ethylene diamine triacetic acid, dihydroxyethyl ethylenediamine diacetic acid, hydroxyethyl iminodiacetic acid, and the like), and the like in order to prevent contamination over time.

The undercoat layer is formed using well-known coating methods. The coating amount (solid content) of the undercoat layer is preferably in a range of 0.1 mg/m² to 100 mg/m² and more preferably in a range of 1 mg/m² to 30 mg/m².

<Protective Layer>

The lithographic printing plate precursor according to the embodiment of the disclosure preferably has a protective layer (in some cases, also referred to as the overcoat layer) on the image-recording layer. The protective layer has a function of suppressing image formation-inhibiting reactions caused by the shielding of oxygen and additionally has a function of preventing the generation of damage in the image-recording layer and abrasion prevention during exposure using high-illuminance lasers.

Protective layers having the above-described characteristics are described in, for example, the specification of U.S. Pat. No. 3,458,311A and JP1980-049729B (JP-S55-049729B). As poor oxygen-transmissible polymers that can be used for the protective layer, it is possible to appropriately select and use any one of water-soluble polymers and water-insoluble polymers, and, if necessary, it is also possible to use two or more polymers in a mixed follii. Specific examples thereof include polyvinyl alcohols, modified polyvinyl alcohols, polyvinyl pyrrolidone, water-soluble cellulose derivatives, poly(meth)acrylonitrile, and the like.

As the modified polyvinyl alcohols, acid-modified polyvinyl alcohols having carboxy groups or sulfo groups are preferably used. Specific examples thereof include modified-polyvinyl alcohols described in JP2005-250216A and JP2006-259137A.

The protective layer preferably includes inorganic lamellar compounds in order to enhance oxygen-shielding properties. The inorganic lamellar compounds refer to particles having thin flat plate shapes, and examples thereof include mica groups such as natural mica and synthetic mica, talc represented by Formula $3MgO.4SiO.H_2O$, taeniolite, montmorillonite, saponite, hectorite, zirconium phosphate, and the like.

The inorganic lamellar compounds that can be preferably used are mica compounds. Examples of mica compounds include mica groups such as natural mica and synthetic mica represented by Formula: $A(B, C)_{2-5}D_4O_{10}(OH, F, O)_2$ [here, A is any of K, Na, or Ca, B and C are any of Fe (II), Fe (III), Mn, Al, Mg, and V, and D is Si or Al.].

In the mica groups, examples of natural mica include white mica, soda mica, gold mica, black mica, and lepidolite. Examples of synthetic mica include non-swelling mica such as fluorphlogopite $KMg_3(AlSi_3O10)F_2$, potassium tetrasilic mica $KIVIg_{2.5}(Si_4O_{10})F_2$, and, Na tetrasilylic mica $NaMg_{2.5}(Si_4O_{10})F_2$, swelling mica such as Na or Li taeniolite $(Na, Li)Mg_2Li(Si_4O_{10})F_2$, montmorillonite-based Na or Li hectorite $(Na, Li)_{1/8}Mg^{2/5}Li_{1/8}(Si_4O_{10})F_2$, and the like. Furthermore, synthetic smectite is also useful.

Among the above-described mica compounds, fluorine-based swelling mica is particularly useful. That is, swelling synthetic mica has a laminate structure consisting of unit crystal lattice layers having a thickness in a range of approximately 10A to 15A (1A is equal to 0.1 mu), and metal atoms in lattices are more actively substituted than in any other clay minerals. As a result, positive charges are deficient in the lattice layers, and positive ions such as $Li^+$, $Na^+$, $Ca^{2+}$, and $Mg^{2+}$ are adsorbed between the layers in order to compensate for the deficiency. Positive ions interposed between the layers are referred to as exchangeable positive ions and are exchangeable with various positive ions. Particularly, in a case in which the positive ions between the layers are $Li^+$ and $Na^+$, the ionic radii are small, and thus the bonds between lamellar crystal lattices are weak, and mica is significantly swollen by water. In a case in which shear is applied in this state, mica easily cleavages and forms a stable sol in water. The above-described tendency of swelling synthetic mica is strong, and the swelling synthetic mica is particularly preferably used.

From the viewpoint of diffusion control, regarding the shapes of the mica compounds, the thickness is preferably thin, and the planar size is preferably large as long as the smoothness and active light ray-transmitting properties of coated surfaces are not impaired. Therefore, the aspect ratio is preferably 20 or higher, more preferably 100 or higher, and particularly preferably 200 or higher. The aspect ratio is the ratio of the long diameter to the thickness of a particle and can be measured from projection views obtained from the microphotograph of the particle. As the aspect ratio increases, the obtained effect becomes stronger.

Regarding the particle diameters of the mica compound, the average long diameter thereof is preferably in a range of 0.3 μm to 20 μm, more preferably in a range of 0.5 μm to 10 μm, and particularly preferably in a range of 1 μm to 5 μm. The average thickness of the particles is preferably 0.1 μm or smaller, more preferably 0.05 μm or smaller, and particularly preferably 0.01 μm or smaller. Specifically, for example, in the case of swelling synthetic mica which is a typical compound, a preferred aspect has a thickness in a range of approximately 1 nm to 50 nm and a surface size (long diameter) in a range of approximately 1 μm to 20 μm.

The content of the inorganic lamellar compound is preferably in a range of 0% by mass to 60% by mass and more preferably in a range of 3% by mass to 50% by mass of the total solid content of the protective layer. Even in a case in which multiple kinds of inorganic lamellar compounds are jointly used, the total amount of the inorganic lamellar compounds is preferably the above-described content. Within the above-described range, the oxygen-shielding properties improve, and a favorable sensitivity can be obtained. In addition, the degradation of the ink-absorbing properties can be prevented.

The protective layer may include well-known additives such as a plasticizer for imparting flexibility, a surfactant for improving coating properties, and inorganic particles for controlling sliding properties on the surface. In addition, the sensitization agent described in the section of the image-recording layer may be added to the protective layer.

The protective layer is formed using a well-known coating method. The coating amount of the protective layer (solid content) is preferably in a range of 0.01 $g/m^2$ to 10 $g/m^2$, more preferably in a range of 0.02 $g/m^2$ to 3 $g/m^2$, and particularly preferably in a range of 0.02 $g/m^2$ to 1 $g/m^2$.

(Method for Producing Lithographic Printing Plate)

A lithographic printing plate can be produced by exposing the lithographic printing plate precursor of the embodiment of the present disclosure in an image shape to carry out a development process.

A method for producing a lithographic printing plate according to an embodiment of the present disclosure preferably includes a step of exposing the lithographic printing plate precursor according to the embodiment of the present disclosure in an image shape and forming an exposed portion and a non-exposed portion (hereinafter, also referred to as the "exposure step") and a step of removing the non-exposed portion by supplying at least one of printing ink or dampening water (hereinafter, also referred to as the "on-machine development step").

In addition, the method for producing a lithographic printing plate according to the embodiment of the present disclosure preferably includes a step of exposing the lithographic printing plate precursor according to the embodiment of the present disclosure including the polymerization initiator and the polymerizable compound in an image shape using a laser and a step of removing a non-exposed portion in the image-recording layer using a one-bath developer having a pH of 2 to 11.

Hereinafter, regarding the method for producing a lithographic printing plate according to the embodiment of the present disclosure and a lithographic printing method according to an embodiment of the present disclosure, preferred aspects of the respective steps will be sequentially described. Meanwhile, the lithographic printing plate precursor of the embodiment of the present disclosure can also be developed using a developer.

<Exposure Step>

The method for producing a lithographic printing plate according to the embodiment of the present disclosure preferably includes an exposure step of exposing the lithographic printing plate precursor according to the embodiment of the present disclosure in an image shape and forming an exposed portion and a non-exposed portion. The lithographic printing plate precursor according to the embodiment of the present disclosure is preferably exposed in an image shape by laser exposure through a transparent original image having a linear image, a halftone dot image, or the like or by laser light exposure according to digital data.

As the wavelength of a light source, a range of 750 nm to 1,400 nm is preferably used. The light source having a wavelength in a range of 750 nm to 1,400 mm is preferably a solid-state laser or a semiconductor laser that radiates infrared rays. Regarding an infrared laser, the output is preferably 100 mW or more, the exposure time per pixel is preferably 20 microseconds or shorter, and the irradiation energy amount is preferably 10 mJ/cm$^2$ to 300 mJ/cm$^2$. In addition, in order to shorten the exposure time, a multibeam laser device is preferably used. The exposure mechanism may be any one of an in-plane drum method, an external surface drum method, a flat head method, or the like.

The image exposure can be carried out using a platesetter or the like and an ordinary method. In the case of on-machine development, image exposure may be carried out on a printer after the lithographic printing plate precursor is mounted on the printer.

<On-Machine Development Step>

The method for producing a lithographic printing plate according to the embodiment of the present disclosure preferably includes an on-machine development step of removing the non-exposed portion by supplying at least one of printing ink or dampening water in this order.

In addition, the method for producing a lithographic printing plate according to the embodiment of the present disclosure may be carried out using a development method using a developer (developer treatment method).

Hereinafter, the on-machine development method will be described.

—On-Machine Development Method—

In the on-machine development method, a lithographic printing plate is preferably produced by supplying oil-based ink and an aqueous component to the lithographic printing plate precursor exposed in an image shape on a printer and removing an image-forming layer in a non-image area.

That is, in a case in which the lithographic printing plate precursor is exposed in an image shape and then mounted as it is in a printer without carrying out any development process or the lithographic printing plate precursor is mounted in a printer, then, exposed in an image shape on a printer, and subsequently supplied with oil-based ink and an aqueous component to carry out printing, in an initial stage in the middle of printing, a non-cured image-forming layer in a non-image area is dissolved or dispersed by any or both of the supplied oil-based ink and aqueous component so as to be removed, and the hydrophilic surface is exposed in the removed portion. On the other hand, in an exposed portion, an image-forming layer cured by exposure forms an oil-based ink-receiving portion having a lipophilic surface. Any of the oil-based ink or the aqueous component may be supplied to the surface of the plate in the beginning; however, from the viewpoint of preventing the aqueous component from being contaminated by a component of the image-forming layer from which the aqueous component is removed, the oil-based ink is preferably supplied in the beginning. In the above-described manner, the lithographic printing plate precursor is on-machine-developed on the printer and is used as it is for printing a number of pieces of paper. As the oil-based ink and the aqueous component, ordinary printing ink and ordinary dampening water for lithographic printing are preferably used.

As the laser used to expose the lithographic printing plate precursor according to the embodiment of the present disclosure including the polymerization initiator and the polymerizable compound, a light source having a wavelength of 300 nm to 450 nm or 750 nrn to 1,400 nm is preferably used. In the case of a light source having a wavelength of 300 nm to 450 nm, a lithographic printing plate precursor containing a sensitizing dye having a maximum absorption in this wavelength range in the image-recording layer is preferably used, and, as a light source having a wavelength of 750 to 1,400 nm, the above-described light source is preferably used. As a light source having a wavelength of 300 nm to 450 nm, a semiconductor laser is preferred.

As the one-bath developer having a pH of 2 to 11, a well-known developer can be used, and, for example, a developer having a pH of 2 to 11 containing at least one of a surfactant or a water-soluble polymer compound is exemplified. In a development process using a strong alkaline developer of the related art, it was necessary to remove the protective layer by a pre-water washing step, subsequently, carry out alkali development, remove an alkali by water washing in a post water washing step, carry out a gum liquid process, and dry a lithographic printing plate precursor in a drying step. In the case of using the developer containing a surfactant and a water-soluble polymer compound, it is possible to carry out development and the gum liquid process at the same time. Therefore, the post water washing step is not particularly necessary, and it is possible to carry out the drying step after development and the gum liquid process are carried out using one liquid. Furthermore, the removal of the protective layer can also be carried out at the same time as development and the gum liquid process, and thus the pre-water washing step is also not particularly necessary. After the development process, it is preferable to remove the surplus developer using a squeeze roller or the like and then dry the lithographic printing plate precursor.

<Printing Step>

The lithographic printing method according to an embodiment of the present disclosure includes a printing step of printing a recording medium by supplying printing ink to the lithographic printing plate on-machine developed in the on-machine development step.

The printing ink is not particularly limited, and a variety of well-known inks can be used as desired. In addition, as the printing ink, oil-based ink or ultraviolet-curable ink (UV ink) is preferably exemplified, and UV ink is more preferably exemplified.

In addition, in the printing step, dampening water may be supplied as necessary.

In addition, the printing step may be successively carried out after the on-machine development step without stopping the printer.

The recording medium is not particularly limited, and a well-known recording medium can be used as desired.

In the method for producing the lithographic printing plate from the lithographic printing plate precursor according to the embodiment of the present disclosure and the lithographic printing method according to the embodiment of the present disclosure, the full surface of the lithographic printing plate precursor may be heated as necessary before exposure, in the middle of exposure, or during a period of time from exposure to development. Such heating accelerates an image-forming reaction in the image-forming layer and generates an advantage of the improvement in sensitivity or printing resistance, the stabilization of sensitivity, or the like. Heating before development is preferably carried out in a mild condition of 150° C. or lower. In the above-described aspect, it is possible to prevent a problem of the curing of the non-image area. For heating after development, an extremely strong condition is preferably used, and a range of 100° C. to 500° C. is preferred. In the above-described range, a sufficient image-strengthening action is obtained, and it is possible to suppress a problem of the deterioration of the support or the thermal decomposition of the image area.

(Color-Developing Composition)

A color-developing composition according to an embodiment of the present disclosure includes a dye compound having a decomposable group that is decomposed by an acid, heat, or both and a structure in which decomposition of the decomposable group opens a ring or desorbs a leaving group (specific dye compound) and an electron-donating polymerization initiator.

The specific dye compound and the electron-donating polymerization initiator in the color-developing composition according to the embodiment of the present disclosure are identical to the specific dye compound and the electron-donating polymerization initiator in the image-recording layer of the lithographic printing plate precursor, and preferred aspects thereof are also identical thereto.

In addition, the color-developing composition according to the embodiment of the present disclosure preferably contains an infrared absorber.

The infrared absorber in the color-developing composition is identical to the infrared absorber in the image-recording layer of the lithographic printing plate precursor, and a preferred aspect thereof is also identical thereto.

Furthermore, the color-developing composition according to the embodiment of the present disclosure may further contain at least one selected from the group consisting of an electron-receiving polymerization initiator, a polymer particle, a polymerizable compound, a binder polymer, a chain transfer agent, a low-molecular-weight hydrophilic compound, a sensitizing agent, or a well-known solvent. Preferred aspects of these compounds are identical to the preferred aspects of the respective compounds in the lithographic printing plate precursor.

In addition, the color-developing composition according to the embodiment of the present disclosure may further contain a well-known additive that is generally used in the color-developing composition according to the purpose.

The contents of the respective components included in the color-developing composition according to the embodiment of the present disclosure correspond to the contents of the respective components included in the image-recording layer of the above-described lithographic printing plate precursor read as the amounts of solid contents in the color-developing composition.

The respective components of the color-developing composition according to the embodiment of the present disclosure are dissolved or dispersed in an appropriate solvent to prepare a coating fluid, and the coating fluid is applied to and dried on an appropriate support or the like to form a color-developing composition film, thereby preferably producing an image-forming material. As the image-forming material, a lithographic printing plate precursor, a printed-wiring board, a color filter, a photo mask, an image-forming material for which color development by image exposure such as ink jet or 3D modeling is used, and an image-forming material for which color development and polymerization curing are used are preferably exemplified.

The image-forming material in which the color-developing composition according to the embodiment of the disclosure is used develops color by being heated or exposed to a light source that radiates an infrared ray. Heating means is not particularly limited, and well-known heating means can be used, and examples thereof include a heater, an oven, a hot plate, an infrared lamp, an infrared laser, and the like. As the light source, a solid-state laser, a semiconductor laser, and the like which radiate an infrared ray are preferably exemplified.

EXAMPLES

Hereinafter, the present embodiment will be described in detail using examples, but the present embodiment is not limited thereto. For polymer compounds, unless particularly otherwise described, the molecular weight refers to the weight-average molecular weight (Mw) converted to a polystyrene equivalent value by the gel permeation chromatography (GPC) method, and the ratio of a repeating unit refers to the molar percentage. In addition, "parts" and "%" indicate "parts by mass" and "% by mass" unless particularly otherwise described.

In addition, dye compounds 1, 2, 4, 5, 7, 8, and 13 used in examples are the same compound as the above-described dye compounds 1, 2, 4, 5, 7, 8, and 13, and electron-donating polymerization initiators B-1 to B-5 are the same composition as the above-described electron-donating polymerization initiators B-1 to B-5.

Synthesis examples of the dye compounds will be described below. Other dye compounds also can be synthesized in the same manner by appropriately changing a raw material or a reaction intermediate.

<Synthesis of Dye Compound 1>

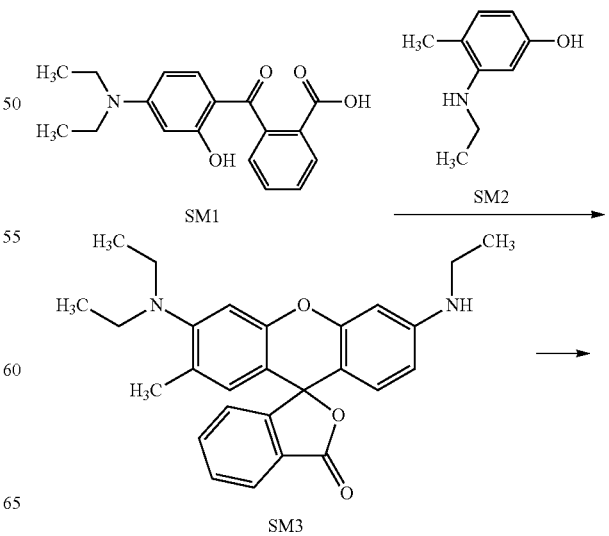

-continued

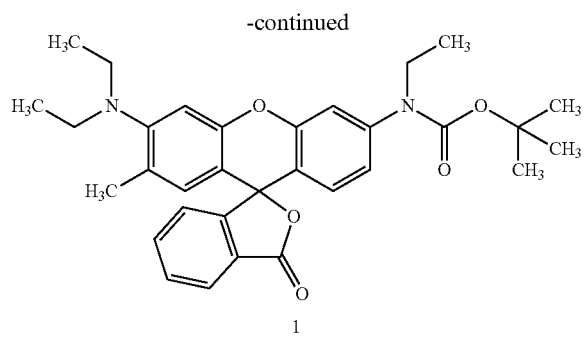

95% Sulfuric acid (40 mL), 2-(4-diethylamino-2-hydroxybenzoyl) benzoic acid (compound SM1) (3.1 g, 10 mmol), and 3-ethylamino-p-cresol (compound SM2) (1.5 g, 10 mmol) were added to a 200 mL three-neck flask and were reacted with each other at 140° C. for five hours. After the reaction, the reaction product was cooled to 0° C., and ice water (40 mL) was added thereto.

A 10% sodium hydroxide aqueous solution was added thereto so that the pH reached 6 to 7, and the generated precipitate was recrystallized using dichloromethane and hexane, thereby obtaining a compound SM3 (2.0 g, yield: 47%).

A compound (2.0 g, 4.7 mmol) and di-tert-butyl dicarbonate (1.2 g, 5.6 mmol) were dissolved in tetrahydrofuran (THF, 40 mL) in a 100 mL eggplant flask and then reacted with each other for three hours. After the completion of the reaction was confirmed by TLC, the solvent was distilled away. The obtained dried substance was recrystallized from ethyl acetate, and the obtained solid was dried for 48 hours using a blast dryer set to 50° C., thereby obtaining a dye compound 1 (2.2 g, yield: 89%).

Examples 1 to 7 and Comparative Examples 1 to 3

1. Production of Infrared Ray-Sensitive Color-Developing Composition

<Production of Support>

In order to remove rolling oil on the surface of a 0.3 mm-thick aluminum plate (material JIS A 1050), a defatting process was carried out thereon using a 10% by mass aqueous solution of sodium aluminate at 50° C. for 30 seconds, and then the surface of the aluminum plate was grained using three implanted nylon brushes having a hair diameter of 0.3 mm and a suspension of pumice having a median diameter of 25 μm and water (specific gravity: 1.1 g/cm³) and well washed with water. The aluminum plate was etched by being immersed in a 25% by mass aqueous solution of sodium hydroxide at 45° C. for nine seconds, was washed with water, then, was further immersed in a 20% by mass aqueous solution of nitric acid at 60° C. for 20 seconds, and was washed with water. The etched amount of the grained surface was approximately 3 g/m².

Next, an electrochemical roughening process was continuously carried out thereon using an alternating current voltage of 60 Hz. An electrolytic solution was a 1% by mass aqueous solution of nitric acid (including 0.5% by mass of aluminum ions.), and the liquid temperature was 50° C. The electrochemical roughening process was carried out thereon using an alternating current power supply waveform in which the time TP taken for the current value to reach the peak from zero was 0.8 msec and the duty ratio was 1:1, and the electrochemical roughening process was carried out using a trapezoidal rectangular wave alternating current and a carbon electrode as a counter electrode. As an auxiliary anode, ferrite was used. The current density was 30 A/dm² in terms of the peak value of the current, and 5% of the current coming from the power supply was divided into the auxiliary anode. Regarding the quantity of electricity during nitric acid electrolysis, the quantity of electricity was 175 C/dm² in a case in which the aluminum plate served as the positive electrode. After that, the plate was washed with water by means of spraying.

Subsequently, an electrochemical roughening process was carried out thereon using the same method as nitric acid electrolysis in a 0.5% by mass aqueous solution of hydrochloric acid (including 0.5% by mass of aluminum ions.) and an electrolytic solution having a liquid temperature of 50° C. under a condition of the quantity of electricity of 50 C/dm² in a case in which the aluminum plate served as the positive electrode, and then, the plate was washed with water by means of spraying.

Next, 2.5 g/m² of a direct current anodized film was formed on the aluminum plate at a current density of 15 A/dm² using a 15% by mass aqueous solution of sulfuric acid (including 0.5% by mass of aluminum ions.) as an electrolytic solution and then washed with water and dried, thereby producing a support A. The average pore diameter in the surface layer of the anodized film (surface average pore diameter) was 10 nm.

The pore diameter in the surface layer of the anodized film was measured using a method in which the surface was observed an ultrahigh resolution SEM (S-900 manufactured by Hitachi, Ltd.) at a relatively low acceleration voltage of 12 V at a magnification of 150,000 times without carrying out a vapor deposition process or the like for imparting conductive properties, 50 pores were randomly extracted, and the average value was obtained. The standard deviation error was ±10% or less.

After that, in order to ensure the hydrophilicity of a non-image area, a silicate process was carried out on the support A at 60° C. for 10 seconds using a 2.5% by mass aqueous solution of No. 3 sodium silicate, and the support was washed with water, thereby producing a support B. The attached amount of Si was 10 mg/m². The center line average roughness (Ra) of the support B was measured using a needle having a diameter of 2 μm and turned out to be 0.51 μm.

A support C was produced in the same manner as in the method for producing the support A except for the fact that, in the production of the support A, the electrolytic solution in the formation of the direct current anodized film was changed to an aqueous solution of 22% by mass of phosphoric acid. The average pore diameter of the surface layer of the anodized film (surface average pore diameter) was measured using the same method as described above and found out to be 25 nm.

After that, a silicate process was carried out on the support C using an aqueous solution of 2.5% by mass of No. 3 silicate soda at 60° C. for 10 seconds in order to ensure the hydrophilicity of a non-image area and then washed with water, thereby producing a support D. The amount of Si attached was 10 mg/m². The center line average roughness (Ra) of the support D was measured using a needle having a diameter of 2 μm and found out to be 0.52

<Formation of Infrared Ray-Sensitive Color-Developing Composition Films>

Infrared ray-sensitive color-developing compositions having the following composition were respectively prepared, applied onto the aluminum support B by means of bar coating so that the dried coating amount reached 1.0 mg/m², and dried in an oven at 120° C. for 40 seconds, thereby producing infrared ray-sensitive color-developing composition films for Examples 1 to 7 and Comparative Examples 1 to 3 respectively.

—Composition of infrared ray-sensitive color-developing composition—

Polymethyl methacrylate (Mw: 12,000): 0.53 parts by mass
Sodium tetraphenylborate salt: 0.010 parts by mass
Dye compound shown in Table 1: 0.050 parts by mass
Electron-receiving polymerization initiator (I-1): 0.040 parts by mass
Surfactant (W-1): 0.008 parts by mass
2-Butanone: 11.3 parts by mass

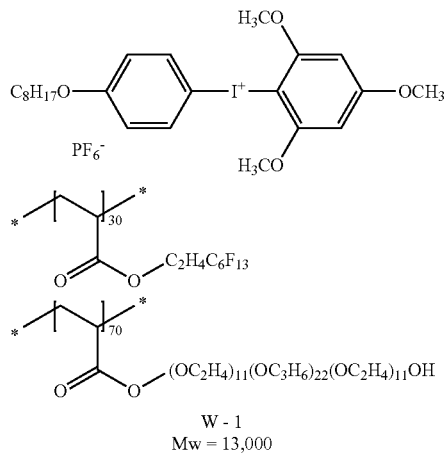

In the structures, suffixes on the lower right side of the parentheses of individual constituent units represent the content ratios (mass ratios).

2. Evaluation of Infrared Ray-Sensitive Color-Developing Composition (1) Color Developability The obtained infrared ray-sensitive color-developing composition film was exposed in Trendsetter3244VX equipped with a water cooling-type 40 W infrared semiconductor laser manufactured by Creo Inc. under conditions of an output of 11.7 W, an external surface drum rotation speed of 250 rpm, and a resolution of 2,400 dpi (dots per inch, 1 inch is equal to 25.4 mm). The exposure was carried out in an environment of 25° C. and 50% RH.

The color development of the infrared ray-sensitive color-developing composition was measured immediately after the exposure and after two-hour storage in a dark room (25° C.) after the exposure. The color development was measured using a spectrophotometer CM2600d and operation software CM-S100W that are manufactured by Konica Minolta Sensing Americas, Inc. and a specular component exclude (SCE) method. The color developability was evaluated by a difference ΔL between an L* value of the exposed portion and an L* value (brightness) of the non-exposed portion using L* values of the L*a*b* color space. As the value of ΔL increases, the color developability becomes more favorable. The evaluation results are shown in Table 1.

(2) Temporal Fading-Suppressing Property

A temporal fading percentage was computed from the following expression using the value ΔL (0 h) of ΔL immediately after the exposure and the value ΔL (2 h) of ΔL after two hours, which were obtained as described above. As the temporal fading percentage decreases, the degree of fading becomes smaller, and the temporal fading-suppressing property becomes more favorable.

Temporal fading percentage (%)=(ΔL(0h)−ΔL(2h))/ΔL(0h)×100

TABLE 1

| | Dye compound (parts by mass) | Group after decomposition (Hammett value) | Electron-donating polymerization initiator (parts by mass) | Color developability ΔL (after exposure 0 h) | Temporal fading-suppressing property Fading percentage (%) |
|---|---|---|---|---|---|
| Example 1 | 1 (0.040) | NHEt (−0.61) | B-1 (0.030) | 6.0 | 5 |
| Example 2 | 2 (0.035) | NHEt (−0.61) | B-2 (0.030) | 5.8 | 0 |
| Example 3 | 4 (0.029) | OH (−0.37) | B-1 (0.030) | 5.6 | 0 |
| Example 4 | 5 (0.033) | NH₂ (−0.66) | B-5 (0.030) | 5.1 | 5 |
| Example 5 | 7 (0.040) | OH (−0.37) | B-2 (0.040) | 4.3 | 0 |
| Example 6 | 8 (0.035) | OH (−0.37) | B-3 (0.035) | 4.6 | 0 |
| Example 7 | 13 (0.035) | OH (−0.37) | B-3 (0.035) | 5.8 | 0 |
| Comparative Example 1 | 1 (0.030) | NHEt (−0.61) | — | 2.3 | 0 |
| Comparative Example 2 | R1 (0.030) | — | B-1 (0.030) | 1.5 | 40 |
| Comparative Example 3 | R2 (0.030) | — | B-1 (0.025) | 4.5 | 35 |

From the results shown in Table 1, it is found that the color-developing composition according to the embodiment of the present disclosure described in the examples is superior to the color-developing compositions of the comparative examples in terms of the color developability and the temporal fading-suppressing property.

Et in Table 1 represents an ethyl group.

In addition, the dye compounds R1 and R2 shown in Table 1 are as illustrated below.

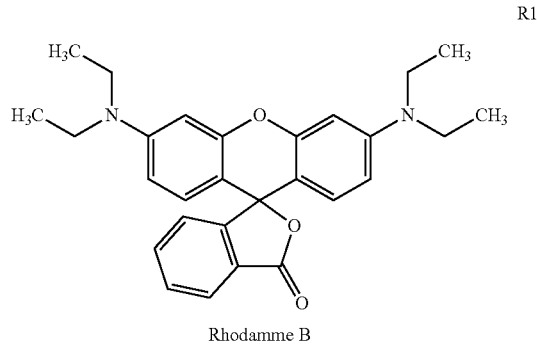

Rhodamme B

-continued

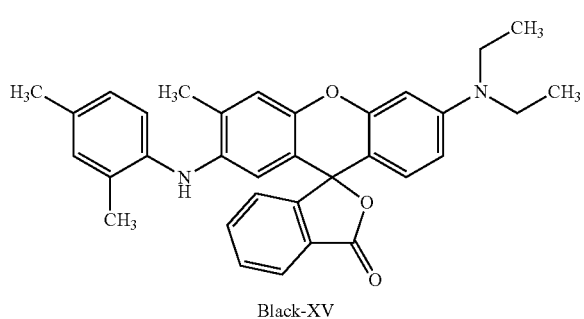

Black-XV

<Coating Fluid for Undercoat Layer (1)>

---

Polymer (P-1) [the following structure]: 0.18 parts
Hydroxyethyl iminodiacetic acid: 0.10 parts
Water: 61.4 parts

---

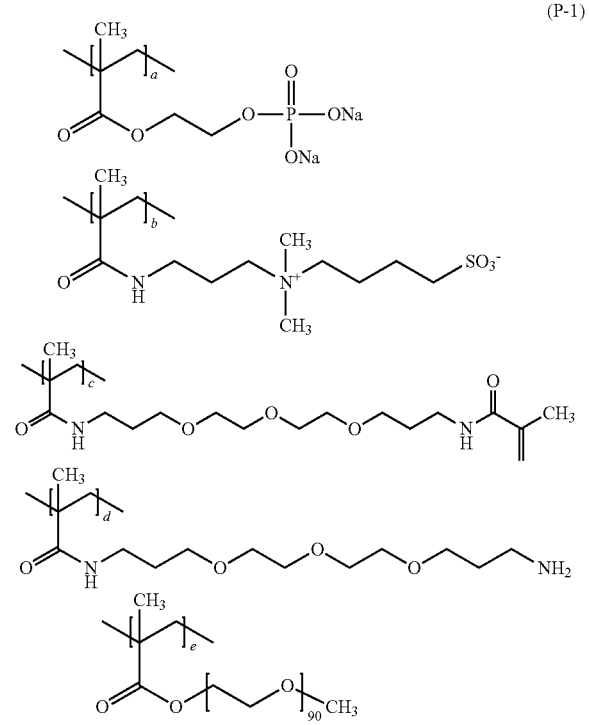

a/b/c/d/e = 14.2/71.8/8.9/0.1/5.0 (% by mass)
a/b/c/d/e = 19.0/72.8/7.7/0.1/0.4 (% by mol)
Weight average molecular weight = 200,000

A method for synthesizing the polymer P-1 will be described below.

(Synthesis of Monomer M-1)

ANCAMINE 1922A (diethylene glycol di(aminopropyl) ether, manufactured by Air Products) (200 g, 0.91 mol), distilled water (435 g), and methanol (410 g) were added to a 3 L three-neck flask and cooled to 5° C. Next, benzoic acid (222.5 g, 1.82 mol) and 4-hydroxy-2,2,6,6-tetramethylpiperidine-1-oxyl (4-OH-TEMPO) (25 mg, 0.15 mmol) were added thereto, and a methacrylic anhydride (280 g, 1.82 mmol) was added dropwise thereto so that the inner temperature of the reaction liquid reached 10° C. or lower. The reaction liquid was stirred at 5° C. for six hours and, subsequently, stirred at 25° C. for 12 hours, and then phosphoric acid (70 g) was added thereto so as to adjust the pH to 3.3. The reaction liquid was moved to a 10 L stainless steel beaker, ethyl acetate (3.7 L), methyl-tert butyl ether (MTBE) (1.5 L), and distilled water (0.65 L) were added thereto, and the components were strongly stirred and then left to stand. The upper layer (organic layer) was disposed of, then, ethyl acetate (1.8 L) was added thereto, the components were strongly stirred and then left to stand, and the upper layer was disposed of. Furthermore, ethyl acetate (1.5 L) was added thereto, the components were strongly stirred and then left to stand, and the upper layer was disposed of. Next, MTBE (1.6 L) was added thereto, the components were strongly stirred and then left to stand, and the upper layer was disposed of 4-OH-TEMPO (62.5 mg, 0.36 mmol) was added to the obtained aqueous solution, thereby obtaining an aqueous solution of a monomer M-1 (1.2 kg, 20.1% by mass in terms of the solid content).

(Purification of Monomer M-2)

LIGHT ESTER P-1M (2-methacryloyloxyethyl acid phosphate, manufactured by Kyoeisha Chemical Co., Ltd.) (420 g), diethylene glycol dibutyl ether (1,050 g), and distilled water (1,050 g) were added to a separating funnel, strongly stirred, and then left to stand. The upper layer was disposed of, diethylene glycol dibutyl ether (1,050 g) was added thereto, and the components were strongly stirred and then left to stand. The upper layer was disposed of, thereby obtaining an aqueous solution of a monomer M-2 (1.3 kg, 10.5% by mass in terms of the solid content).

(Synthesis of Polymer P-1)

Distilled water (600.6 g), the aqueous solution of the monomer M-1 (33.1 g), and a monomer M-3 described below (46.1 g) were added to a 3 L three-neck flask and heated to 55° C. in a nitrogen atmosphere. Next, a dropwise addition liquid A described below was added dropwise thereto for two hours, the components were stirred for 30 minutes, then, VA-046B (manufactured by Wako Pure Chemical Corporation) (3.9 g) was added thereto, and the components were heated to 80° C. and stirred for 1.5 hours. The reaction liquid was returned to room temperature (25° C., which shall apply below), and then an aqueous solution of 30% by mass of sodium hydroxide (175 g) was added thereto, thereby adjusting the pH to 8.3. Next, 4-OH-TEMPO (152.2 mg) was added thereto, and the components were heated to 53° C. A methacrylic anhydride (66.0 g) was added thereto, and the components were stirred at 53° C. for three hours. The components were returned to room temperature, then, the reaction liquid was moved to a 10 L stainless steel beaker, MTBE (1,800 g) was added thereto, the components were strongly stirred and then left to stand, and the upper layer was disposed of A washing operation using MTBE (1,800 g) was further repeated twice in the same manner, and then distilled water (1,700 g) and 4-OH-TEMPO (212 mg) were added to the obtained water layer, thereby obtaining a polymer P-1 (4.1 kg, 11.0% in terms of the solid content) as a homogeneous solution. The weight-average molecular weight (Mw) converted to a polyethylene glycol equivalent value by the gel permeation chromatography (GPC) method was 200,000.

—Dropwise Addition Liquid A—

The aqueous solution of the monomer M-1: 132.4 g
The aqueous solution of the monomer M-2: 376.9 g
Monomer M-3 [the following structure]: 184.3 g
BREMMER PME 4000 (manufactured by NOF Corporation): 15.3 g VA-046B (manufactured by Wako Pure Chemical Corporation): 3.9 g
Distilled water: 717.4 g
BREMMER PME 4000: Methoxy polyethylene glycol methacrylate (the number of the oxyethylene unit repeated: 90)
VA-046B: 2,2'-Azobis[2-(2-imidazolin-2-yl)propane] disulfate dihydrate

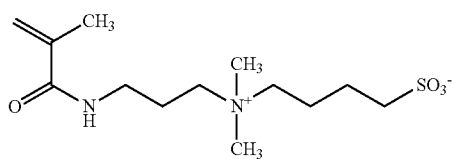

Monomer M-3

<Preparation of Coating Fluid for Image-Recording Layer>

Individual components were added according to the amounts used shown in Table 2, a solvent was added thereto so that the concentration of the solid content reached 7.0% by mass, and the components were mixed together. The amounts (parts) of individual materials added in Table 2 are the amounts of the solid content.

An expression such as "M-1/M-3 (20/45)" in Table 1 indicates that 20 parts of M-1 and 45 parts by M-3 are included.

<Preparation of Coating Fluid for Protective Layer>

| | |
|---|---|
| Inorganic lamellar compound dispersion liquid (1) [illustrated below] | 1.5 parts |
| Six percent by mass aqueous solution of polyvinyl alcohol (CKS50 manufactured by The Nippon Synthetic Chemical Industry Co., Ltd., sulfonic acid-modified, degree of saponification: 99% by mol or higher, degree of polymerization: 300) | 0.55 parts |
| Six percent by mass aqueous solution of polyvinyl alcohol (PVA-405 manufactured by Kuraray Co., Ltd., degree of saponification: 81.5 mol %, degree of polymerization: 500) | 0.03 parts |
| One percent by mass aqueous solution of a surfactant (polyoxyethylene lauryl ether, EMALEX 710, manufactured by Nihon Emulsion Co., Ltd.) | 0.86 parts |
| Ion exchange water | 6.0 parts |

A method for preparing the inorganic lamellar compound dispersion liquid (1) using the coating fluid for a protective layer will be described below.

<Preparation of Inorganic Lamellar Compound Dispersion Liquid (1)>

Synthetic mica (SOMASIF ME-100 manufactured by Co-op Chemical Co., Ltd.) (6.4 g) was added to ion exchange water (193.6 g) and dispersed using a homogenizer until the average particle diameter (laser scattering method) reached 3 The aspect ratio of the obtained dispersed particle was 100 or higher.

Examples 8 to 20 and Comparative Examples 4 to 6

<Production of Lithographic Printing Plate Precursors>

Lithographic printing plate precursors of Examples 8 to 20 and Comparative Examples 4 to 6 were respectively produced using the following method.

The coating fluid for an undercoat layer having the above-described composition was applied onto the support so that the dried coating amount reached 20 mg/m$^2$, thereby forming an undercoat layer. Each coating fluid for an image-recording layer shown in Table 1 was applied onto the undercoat layer by means of bar coating and dried in an oven at 120° C. for 40 seconds, thereby forming an image-recording layer having a dried coating amount of 1.0 g/m$^2$.

As necessary, the coating fluid for a protective layer having the above-described composition was applied onto the image-recording layer by means of bar coating and dried in an oven at 120° C. for 60 seconds, thereby forming a protective layer having a dried coating amount of 0.15 g/m$^2$.

Examples in which the protective layer was formed have an expression of "Present" in the "Protective layer" column in Table 2.

<Evaluation of Lithographic Printing Plate Precursor>

The lithographic printing plate precursors produced as described above were exposed (to an equivalent irradiation energy of 110 mJ/cm$^2$) using Magnus 800 Quantum equipped with an infrared semiconductor laser manufactured by Kodak Japan Ltd. under conditions of an output of 27 W, an external surface drum rotation speed of 450 rpm, and a resolution of 2,400 dpi (dots per inch, 1 inch is equal to 2.54 cm). Exposed images were provided with a solid image and an amplitude modulation screen (AM screen) 3% halftone dot chart.

(1) Color Developability

The obtained lithographic printing plate precursor was exposed under the above-described conditions. The exposure was carried out in an environment of 25° C. and 50% RH.

The color development of the lithographic printing plate precursor was measured immediately after the exposure and after two-hour storage in a dark room (25° C.) after the exposure. The color development was measured using a spectrophotometer CM2600d and operation software CM-S100W that are manufactured by Konica Minolta Sensing Americas, Inc. and a specular component exclude (SCE) method. The color developability was evaluated by a difference ΔL between an L* value of the exposed portion and an L* value of the non-exposed portion using L* values (brightness) of the L*a*b* color space. As the value of ΔL increases, the color developability becomes more favorable.

(2) Temporal Fading-Suppressing Property

A temporal fading percentage was computed from the following expression using the value ΔL (0 h) of ΔL immediately after the exposure and the value ΔL (2 h) of ΔL after two hours, which were obtained as described above. As the temporal fading percentage decreases, the degree of fading becomes smaller, and the temporal fading-suppressing property becomes more favorable.

Temporal fading percentage (%)=(ΔL(0h)−ΔL(2h))/ΔL(0h)×100

(3) Printing Property

The obtained lithographic printing plate precursor was exposed under the above-described conditions and subsequently attached to a cylinder of a kikuban-size (636 mm×939 mm) printer SX-74 manufactured by Heidelberger Druckmaschinen AG with no development process carried out thereon. In the present printer, a non-woven fabric filter and a 100 L-capacity dampening water circulation tank including a temperature controller were connected to each other. Dampening water (80 L) containing 2.0% of dampening water S-Zl (manufactured by Fujifilm Corporation) was prepared in a circulation device, the dampening water and ink were supplied by a standard automatic printing start method using T&K UV OFS K-HS black GE-M (manufactured by T&K TOKA Corporation) as the printing ink, and then printing was carried out on 10,000 pieces of TOKUBISHI art paper (76.5 kg) at a printing rate of 10,000 pieces per hour.

All of the lithographic printing plates obtained from the lithographic printing plate precursors of Examples 8 to 20 imparted printed matters without any problem.

TABLE 2

| | Dye compound (parts) | Group after decomposition (Hammett value) | Electron-donating polymerization initiator (parts) | Infrared absorber (parts) | Electron-receiving polymerization initiator (parts) | Acid color developing agent (parts) | Polymerizable compound (parts) | Polymer particle (parts) | Surfactant (parts) | Binder polymer (parts) | Sensitizing agent (parts) | Hydrophilic compound (parts) | Support | Protective layer | Solvent (mass ratio) | Color developability ΔL (after exposure 0 h) | Temporal fading-suppressing property Fading percentage (%) |
|---|---|---|---|---|---|---|---|---|---|---|---|---|---|---|---|---|---|
| Example 8 | 1 (33) | NHEt (−0.61) | B-1 (36) | K-1 (30) | I-1 (130) | — | M-1/M-3 (20/45) | G-1 (300) | W-1 (8) | (250) | C-1 (10) | T-3 (20) | A | — | S-1/S-2 (15/75) | 5.5 | 0 |
| Example 9 | 2 (41) | NHEt (−0.61) | B-2 (34) | K-1 (25) | I-1 (90) | — | M-2 (110) | G-1 (150) | W-1 (8) | (190) | C-2 (22) | T-1 (30) | A | — | S-3/S-2 (30/70) | 5.1 | 5 |
| Example 10 | 3 (23) | NHEt (−0.61) | B-3 (45) | K-1 (45) | I-1 (35) | — | M-4 (200) | G-1 (305) | W-1 (8) | (230) | — | T-2 (25) | B | — | S-3/S-4 (40/60) | 4.4 | 0 |
| Example 11 | 4 (30) | OH (−0.37) | B-1 (5) | K-2 (38) | I-1 (60) | — | M-2 (226) | O-2 (260) | W-1 (8) | — | C-3 (40) | T-1 (5) | C | Present | S-3/S-4/S-1 (40/40/20) | 4.6 | 5 |
| Example 12 | 5 (34) | NH₂ (−0.66) | B-5 (35) | K-3 (28) | I-2 (60) | — | M-3 (320) | O-2 (450) | W-1 (8) | (180) | — | — | D | Present | S-2/S-5/S-1 (40/10/50) | 4.9 | 0 |
| Example 13 | 6 (22) | NHMe (−0.70) | B-1 (30) | K-3 (45) | I-2 (90) | — | M-4/M-5 (190/40) | G-1 (360) | W-1 (8) | (200) | — | T-3/T-2/T-1 (20/32/10) | A | — | S-1/S-2/S-3 (40/50/10) | 5.2 | 0 |
| Example 14 | 7 (50) | OH (−0.37) | B-2/B-1 (23/10) | K-3 (50) | I-2 (120) | H-1 | M-5 (212) | O-2 (600) | W-1 (8) | — | — | T-3 (15) | B | — | S-4/S-5 (50/50) | 4.6 | 5 |
| Example 15 | 8 (28) | OH (−0.37) | B-3 (50) | K-1 (19) | I-2 (140) | H-2 | M-3 (245) | G-1 (400) | W-1 (8) | (160) | C-1/C-2 (15/5) | — | A | — | S-3/S-4/S-5 (20/30/50) | 4.1 | 0 |
| Example 16 | 9 (30) | OH (−0.37) | B-4 (40) | K-1 (36) | I-3 (50) | H-3 | M-2 (230) | O-2 (250) | W-1 (8) | — | — | — | C | Present | S-3/S-4/S-5 (70/20/10) | 4.6 | 0 |
| Example 17 | 10 (35) | OH (−0.37) | B-5 (36) | K-1 (55) | I-3 (35) | H-4 | M-3 (180) | G-1 (325) | W-1 (8) | (300) | C-2/C-3 (30/5) | T-1/T-2 (5/27) | B | Present | S-1/S-3/S-4/S-5 (60/20/15/5) | 4.2 | 5 |
| Example 18 | 11 (45) | OH (−0.37) | * | K-2 (60) | I-2 (35) | — | M-3/M-4/M-5 90/30/100 | G-2 (300) | W-1 (8) | — | — | T-3 (70) | D | — | S-4/S-5 (50/50) | 5.0 | 0 |
| Example 19 | 12 (34) | OH (−0.37) | (20) B-1 (31) | K-3 (33) | I-3 (150) | — | M-1/M-4 (180/30) | G-1 (410) | W-1 (8) | (90) | C-3 (30) | T-1/T-2/T-3 (5/27/3) | C | Present | S-1/S-2 (70/30) | 4.7 | 0 |
| Example 20 | 13 (39) | OH (−0.37) | B-1 (32) | K-3 (28) | I-3 (40) | — | M-2 (150) | O-2 (273) | W-1 (8) | (236) | — | — | A | — | S-1/S-3 (90/10) | 4.8 | 0 |
| Comparative Example 4 | 1 (30) | NHEt (−0.61) | — | K-1 (35) | I-3 (50) | — | M-3 (190) | G-1 (260) | W-1 (8) | (250) | C-1 (18) | T-3 (40) | A | — | S-1/S-2/S-3 (25/25/50) | 2.5 | 0 |
| Comparative Example 5 | R1 (30) | — | B-1 (45) | K-2 (32) | I-3 (65) | — | M-2/M-3/M-5 (60/60/14) | G-2 (300) | W-1 (8) | — | — | T-2 (15) | B | — | S-2/S-5 (15/85) | 1.0 | 40 |
| Comparative Example 6 | R2 (30) | — | B-1 (35) | K-3 (29) | I-1 (130) | — | M-2 (60/50) | G-1 (300) | W-1 (8) | (210) | — | — | C | — | S-1/S-2/S-4/S-5 (80/10/5/5) | 4.7 | 35 |

From the results shown in Table 2, it is clear that the lithographic printing plate precursor according to the embodiment of the present disclosure described in the examples is superior to the lithographic printing plate precursors of the comparative examples in terms of the color developability and the temporal fading-suppressing property.

* in Table 2 represents that the electron-donating polymerization initiator was derived from K-2 and I-2 and included a tetraphenyl borate anion.

Et in Table 2 represents an ethyl group, and Me represents a methyl group.

In addition, the details of individual compounds shown in Table 2 other than the above-described compounds will be described below.

[Infrared Absorber]

K-1 to K-3: Compounds having the following structure

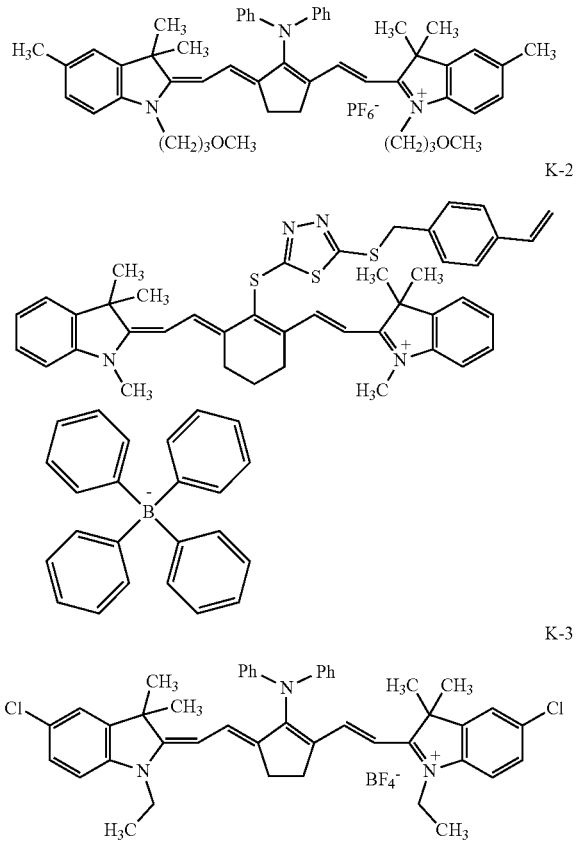

In the structures, Ph represents a phenyl group.

[Electron-Receiving Polymerization Initiator]

I-1 to I-3: Compounds having the following structure

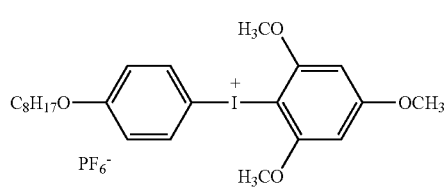

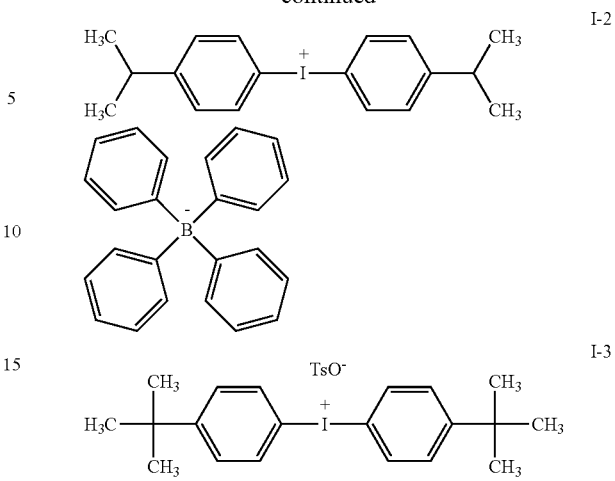

In the structures, TsO⁻ represents a tosylate anion.

[Acid Color Developing Agent]

H-1: S-205 (manufactured by Fukui Yamada Chemical Co., Ltd.)

H-2: GN-169 (manufactured by Yamamoto Chemicals Inc.)

H-3: Black-XV (manufactured by Yamamoto Chemicals Inc.)

H-4: Red-40 (manufactured by Yamamoto Chemicals Inc.)

[Polymerizable Compound]

M-1: Tris(acryloyloxyethyl)isocyanurate, NK ester A-9300, manufactured by Shin-Nakamura Chemical Co., Ltd.

M-2: Dipentaerythritol pentaacrylate, SR-399, manufactured by Sartomer Japan Inc.

M-3: Dipentaerythritol hexaacrylate, A-DPH, manufactured by Shin-Nakamura Chemical Co., Ltd.

M-4: Dipentaerythritol pentaacrylate hexamethylene diisocyanate urethane prepolymer, UA-510H, manufactured by Kyoeisha Chemical Co., Ltd.

M-5: Ethoxylated pentaerythritol tetaracrylate, ATM-4E, manufactured by Shin-Nakamura Chemical Co., Ltd.

[Polymer Particle]

G-1: The following micro gel (1); the coating fluid for an image-recording layer including the polymer particle G-1 (micro gel (1)) was prepared by mixing and stirring a photosensitive liquid obtained by mixing components other than the following micro gel liquid and shown in Table 2 and the following micro gel liquid immediately before being applied so as to obtain a composition shown in Table 2.

G-2: The following polymer particle G-2

—Preparation of Micro Gel Liquid—

Micro gel (1) (polymer particle G-1): 2.640 parts
Distilled water: 2.425 parts

A method for preparing a micro gel (1) used for the micro gel liquid will be described below.

—Preparation of Polyhydric Isocyanate Compound (1)—

Bismuth tris(2-ethylhexanoate) (NEOSTAN U-600, manufactured by Nitto Kasei Co., Ltd.) (43 mg) was added to an ethyl acetate (25.31 g) suspended solution of isophorone diisocyanate (17.78 g, 80 mmol) and the following polyhydric phenol compound (1) (7.35 g, 20 mmol), and the components were stirred. The reaction temperature was set to 50° C. in a case in which the generation of heat settled, and the components were stirred for three hours, thereby obtaining an ethyl acetate solution of a polyhydric isocyanate compound (1) (50% by mass).

Polyhydric Phenol Compound (1)
—Preparation of Micro Gel (1)—
Oil-phase components described below and a water-phase component described below were mixed together and emulsified at 12,000 rpm for 10 minutes using a homogenizer. The obtained emulsion was stirred at 45° C. for four hours, a 10% by mass aqueous solution of 1,8-diazabicyclo[5.4.0]undec-7-ene-octanoic acid salt (U-CAT SA102, manufactured by San-Apro Ltd.) (5.20 g) was added thereto, and the components were stirred at room temperature for 30 minutes and left to stand at 45° C. for 24 hours. Adjustment was made using distilled water so that the concentration of the solid content reached 20% by mass, thereby obtaining a water dispersion liquid of a micro gel (1). The average particle diameter was measured using a light scattering method and found out to be 0.28 μm.

~Oil-Phase Components~
(Component 1) Ethyl acetate: 12.0 g
(Component 2) An adduct obtained by adding trimethylolpropane (6 mol) and xylene diisocyanate (18 mol) and adding methyl single terminal polyoxy ethylene (1 mol, the number of the oxyethylene unit repeated: 90) thereto (a solution of 50% by mass of ethyl acetate, manufactured by Mitsui Chemicals Inc.): 3.76 g
(Component 3) Polyhydric isocyanate compound (1) (as a solution of 50% by mass of ethyl acetate): 15.0 g
(Component 4) An ethyl acetate solution of 65% by mass of dipentaerythritol pentaacrylate (SR-399, Sartomer Japan Inc.): 11.54 g
(Component 5) An ethyl acetate solution of 10% of a sulfonate-type surfactant (BIONINE A-41-C, manufactured by Takemoto Oil & Fat Co., Ltd.): 4.42 g ~Water-Phase Component~
Distilled water: 46.87 g —Preparation of Water Dispersion Liquid of Polymer Particle G-2—
A stirrer, a thermometer, a dropping funnel, a nitrogen introduction pipe, and a reflux cooler were provided to a 1,000 ml four-neck flask, nitrogen gas was introduced thereinto, polyethylene glycol methyl ether methacrylate (PEGMA, the average repeating unit number of ethylene glycol: 50) (10 g), distilled water (200 g), and n-propanol (200 g) were added thereto while carrying out deoxidation by introducing nitrogen gas, and the components were heated until the inner temperature reached 70° C. Next, a mixture obtained by mixing styrene (St) (10 g), acrylonitrile (AN) (80 g), and 2,2'-azobisisobutyronitrile (0.8 g) in advance was added dropwise thereto for one hour. A reaction continued for five hours after the end of the dropwise addition, then, 2,2'-azobisisobutyronitrile (0.4 g) was added thereto, and the inner temperature was increased up to 80° C. Subsequently, 2,2'-azobisisobutyronitrile (0.5 g) was added thereto for six hours. At a stage of continuing the reaction for a total of 20 hours, 98% or more of polymerization had progressed, and a water dispersion liquid (1) of the polymer particle G-2 including PEGMA/St/AN in a mass ratio of 10/10/80 was prepared. The particle size distribution of the polymer particle G-2 had the maximum value at a particle diameter of 150 nm.

The particle size distribution was obtained by capturing an electron micrograph of the polymer particles, measuring the particle diameters of a total of 5,000 particles on the photograph, dividing the range of the obtained particle diameter measurement values from zero to the maximum value into 50 sections using a logarithmic scale, and plotting the appearance frequency of the respective particle diameters. Meanwhile, for a non-spherical particle, the particle diameter value of a spherical particle having the same particle area as the particle area on the photograph was considered as the particle diameter.

(Hydrophilic Compound)
T-1: Tris(2-hydroxyethyl) isocyanurate
T-2: A compound having the following structure
T-3: Hydroxypropyl cellulose, Klucel M, manufactured by Hercules Incorporated (Sensitization Agent)
C-1: A compound having the following structure
C-2: Benzyldimethyloctylammonium.$PF_6$ salt
C-3: A compound having the following structure

[Solvent]
S-1: 2-Butanone (MEK)
S-2: 1-Methoxy-2-propanol (MFG)
S-3: Methanol
S-4: 1-Propanol
S-5: Distilled water The disclosure of JP2017-143870 filed on Jul. 25, 2017 is wholly incorporated into the present specification by reference.

All of documents, patent applications, and technical standards described in the present specification are incorporated into the present specification by reference to approximately the same extent as a case where it is specifically and respectively described that the respective documents, patent applications, and technical standards are incorporated by reference.

What is claimed is:

1. A lithographic printing plate precursor comprising:
an image-recording layer on a support,
wherein the image-recording layer includes a dye compound having a decomposable group that is decomposed by an acid, heat, or both and a structure in which decomposition of the decomposable group opens a ring or desorbs a leaving group and an electron-donating polymerization initiator,
the decomposable group is different from the leaving group,
the decomposable group is different from the ring, and
the decomposable group is a group represented by any of Formula D-1 to Formula D-5,

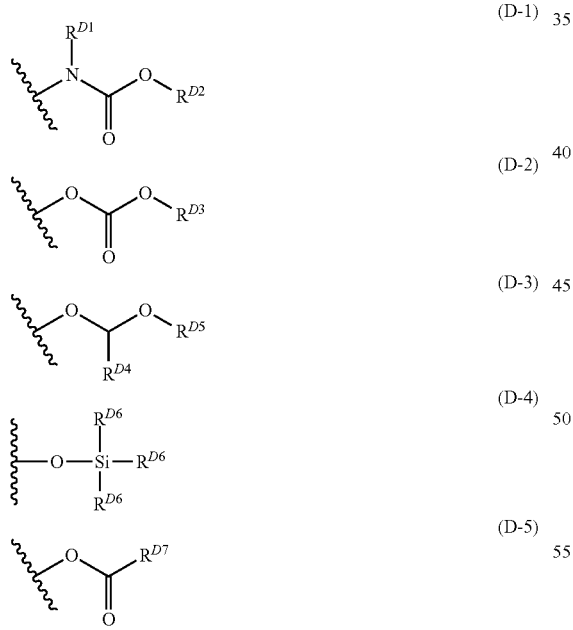

in Formula D-1 to Formula D-5, $R^{D1}$ represents an alkyl group, $R^{D2}$ represents an alkyl group or an aryl group, $R^{D3}$ represents an alkyl group, $R^{D4}$ represents a hydrogen atom or an alkyl group, $R^{D5}$ represents an alkyl group, $R^{D4}$ and $R^{D5}$ may bond to each other to form a ring, $R^{D6}$'s each independently represent an alkyl group or an aryl group, and $R^{D7}$ represents an alkyl group or an aryl group.

2. The lithographic printing plate precursor according to claim 1,
wherein the decomposable group is a group that is decomposed by an acid, heat, or both to generate an amino group or a hydroxy group.

3. The lithographic printing plate precursor according to claim 1,
wherein the structure in which decomposition of the decomposable group opens a ring or desorbs a leaving group is a structure represented by any of Formula 1a to Formula 1d,

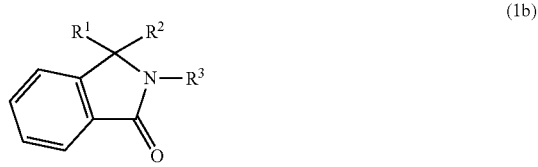

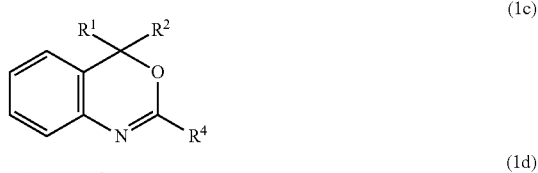

in Formula 1a to Formula 1 d, $R^1$ and $R^2$ represent a portion that is linked to a core structure of the dye compound, $R^3$ and $R^4$ represent an aryl group or a heteroaryl group, $R^5$ represents a hydrocarbon group, and X represents the leaving group.

4. The lithographic printing plate precursor according to claim 1,
wherein the dye compound has a structure represented by any of Formula 3a to Formula 3d as a core structure,

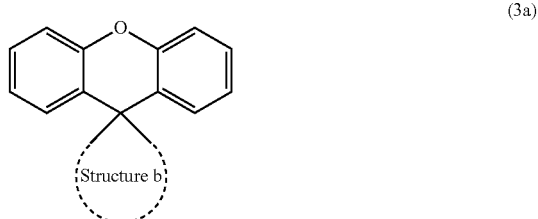

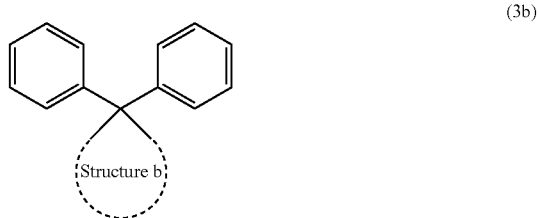

-continued

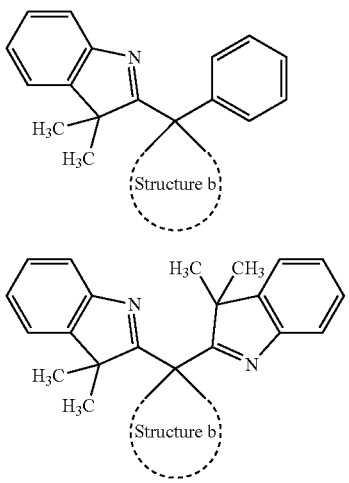

in Formula 3a to Formula 3d, a structure b represents a structure in which a ring is opened by decomposition of the decomposable group, the structure in which a ring is opened by decomposition of the decomposable group is represented by any of Formula 1a to Formula 1 d,

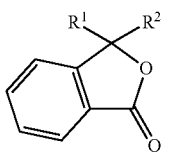

(1a)

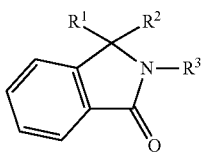

(1b)

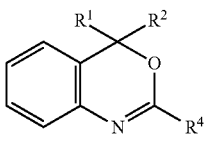

(1c)

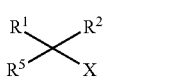

(1d)

in Formula 1a to Formula 1 d, $R^1$ and $R^2$ represent a portion that is linked to a core structure of the dye compound, $R^3$ and $R^4$ represent an aryl group or a heteroaryl group, $R^5$ represents a hydrocarbon group, and X represents the leaving group, and the structures represented by Formula 3a to Formula 3d have one or more decomposable groups on an aromatic ring in Formula 3a to Formula 3d.

5. The lithographic printing plate precursor according to claim 1,
wherein the electron-donating polymerization initiator is a borate compound.

6. The lithographic printing plate precursor according to claim 1,
wherein the image-recording layer further includes an infrared absorber.

7. The lithographic printing plate precursor according to claim 6,
wherein the infrared absorber is a cyanine colorant.

8. The lithographic printing plate precursor according to claim 1,
wherein the image-recording layer further includes an electron-receiving polymerization initiator.

9. The lithographic printing plate precursor according to claim 1,
wherein the image-recording layer further includes a polymer particle.

10. The lithographic printing plate precursor according to claim 1,
wherein the image-recording layer further includes a polymerizable compound.

11. The lithographic printing plate precursor according to claim 1,
wherein the image-recording layer further includes a binder polymer.

12. A method for producing a lithographic printing plate, comprising:
exposing the lithographic printing plate precursor according to claim 1 in an image shape and forming an exposed portion and a non-exposed portion; and
removing the non-exposed portion by supplying at least one of printing ink or dampening water.

13. A color-developing composition comprising:
a dye compound having a decomposable group that is decomposed by an acid, heat, or both and a structure in which decomposition of the decomposable group opens a ring or desorbs a leaving group; and
an electron-donating polymerization initiator,.
wherein the decomposable group is a group represented by any of Formula D-1 to Formula D-5,

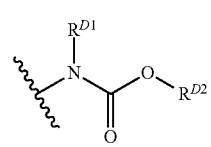

(D-1)

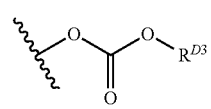

(D-2)

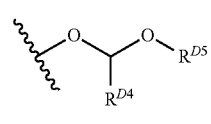

(D-3)

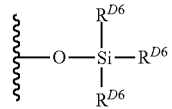

(D-4)

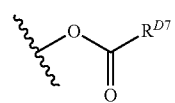

(D-5)

in Formula D-1 to Formula D-5, $R^{D1}$ represents an alkyl group, $R^{D2}$ represents an alkyl group or an aryl group, $R^{D3}$ represents an alkyl group, $R^{D4}$ represents a hydrogen atom or an alkyl group, $R^{D5}$ represents an alkyl group, $R^{D4}$ and $R^{D5}$ may bond to each other to form a ring, $R^{D6}$'s each independently represent an alkyl group or an aryl group, and $R^{D7}$ represents an alkyl group or an aryl group.

14. The lithographic printing plate precursor according to claim 1,
wherein the dye compound is a dye compound having the decomposable group that is decomposed by an acid, heat, or both and a structure in which decomposition of the decomposable group opens a ring.

* * * * *